United States Patent [19]

Mochida

[11] Patent Number: 5,147,607
[45] Date of Patent: Sep. 15, 1992

[54] REACTION VESSEL WITH A ROCKING BASE

[75] Inventor: Ei Mochida, Tokyo, Japan

[73] Assignee: Mochida Pharmaceutical Co., Ltd., Tokyo, Japan

[21] Appl. No.: 619,523

[22] Filed: Nov. 29, 1990

[30] Foreign Application Priority Data

Nov. 30, 1989 [JP] Japan .................. 1-312122

[51] Int. Cl.$^5$ .................. G01N 21/00; G01N 31/22
[52] U.S. Cl. .................. 422/57; 422/58; 422/61; 422/102; 435/810; 436/808
[58] Field of Search .................. 422/56, 58, 61, 101, 422/102, 57, 68.1; 435/805, 810; 436/808

[56] References Cited

U.S. PATENT DOCUMENTS

| | | | |
|---|---|---|---|
| 4,076,562 | 2/1978 | Bradley | 422/102 |
| 4,426,451 | 1/1984 | Columbus | 422/58 |
| 4,714,590 | 12/1987 | Guigan | 422/61 |
| 4,963,498 | 10/1990 | Hillman et al. | 422/102 |
| 4,981,786 | 1/1991 | Dafforn et al. | 422/101 |
| 4,990,075 | 2/1991 | Wogoman | 436/165 |

FOREIGN PATENT DOCUMENTS 0276152 7/1988 European Pat. Off. .

*Primary Examiner*—James C. Housel
*Assistant Examiner*—Jan M. Ludlow
*Attorney, Agent, or Firm*—Burns, Doane, Swecker & Mathis

[57] ABSTRACT

A reaction vessel for microassay is provided. The reaction vessel has a body structure having provided therein at least one reaction unit having a channel having at least one fluid inlet and at least one reagent-immobilized area in the downstream of the fluid inlet. The channel is provided with a vent mechanism, and the reagent-immobilized area has a reagent fixedly immobilized thereto. The results of the assay are indicated in the reagent-immobilized area. The channel may be provided with a reagent-attached area wherein a reagent is tentatively attached so that the reagent may dissolve into the fluid flowing over the area. The channel may be also provided with a fluid sump for retaining the fluid within the reaction vessel. A rocking base allows the vessel to become inclined as the downstream sump moves downward when the fluid moves into the sump. By using the present reaction vessel, an assay at high precision may be carried out by a simple operation.

22 Claims, 20 Drawing Sheets

F I G. 17a
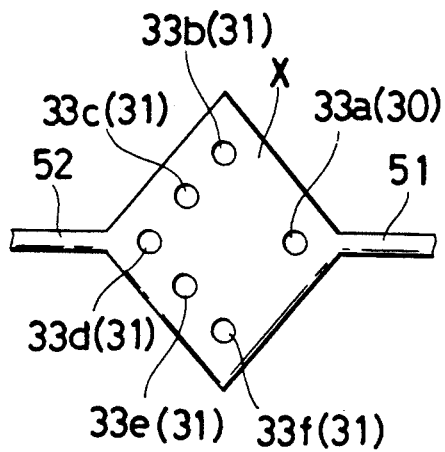
F I G. 17b
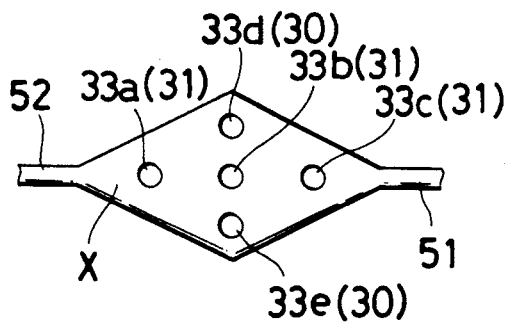
F I G. 17c
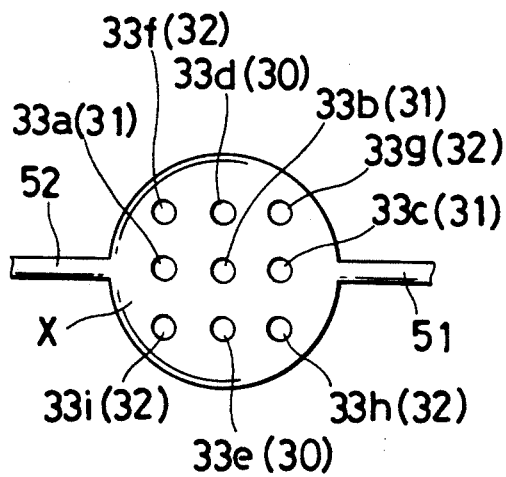

REACTION VESSEL WITH A ROCKING BASE

BACKGROUND OF THE INVENTION

This invention relates to a reaction vessel which may be used for measuring a minute amount of substance present in a living body by a simple and convenient operation.

Microanalysis of a biological substance is often carried out for the purpose of diagnosing various diseases and determining effects of various treatments. A number of assays have been developed one after another ranging from simple and convenient assays to highly sensitive assays realizing a high measurement accuracy. Among these, simplified assays, which require no measuring equipment or reaction system, are finding a wide application owing to their simple operation in such cases wherein qualitative or semi-quantitative measurements are just sufficient to make diagnoses. For example, simplified assays are used for a measurement of glucose in urine and other biochemical tests, as well as pregnancy tests. Recently, simplified assays have also been used for detection of various pathogenic viruses by nucleic acid hybridization with DNA probes.

Typical simplified assays based on immunoreactions (antigen-antibody reactions) include those utilizing an agglutination reaction (i.e. agglutination or non-agglutination) using a latex or red blood cell for their carrier and enzyme immunoassays (EIA) using an enzyme for labelling purposes.

Among the agglutination reactions, those utilizing agglutination-precipitation reaction are conducted in an ampoule having a spherical bottom surface by using red blood cell or analogous synthetic material for their carrier, and their results are evaluated by presence or size of a ring or a spot precipitated inside the spherical bottom surface. These processes may be conveniently carried out with a relatively high measurement sensitivity, but may take a long time for obtaining the results since they are based on precipitation of red blood cells or analogous synthetic materials.

The process utilizing a latex for the agglutination reaction is carried out on a slide by using a latex as their carrier. The results are evaluated after stirring the sample by observing the degree of agglutination. The latex agglutination reaction is not very sensitive, but can be carried out in a short period by a simple operation. Therefore, the latex agglutination reaction is widely employed in such application as pregnancy test wherein a high sensitivity is not necessarily required. The latex agglutination reaction, however, requires much skill for determination of the results, and therefore, those who are capable of making an accurate determination are primarily limited to doctors and laboratory technicians in medical institutions including hospitals and clinics.

The enzyme immunoassays are more sensitive than other simplified assays, but often take a relatively long reaction time for obtaining a high sensitivity. The enzyme immunoassays also suffer from a drawback that troublesome operations are required for B/F (bound/free) separation and an incomplete B/F separation would result in non-specific reactions in the subsequent enzyme reaction step leading to an erroneous evaluation of the results. B/F separation is a separation of an antigen-antibody complex (an antigen bound to an antibody, B) from free antigens or antibodies (F) in the case of an antigen-antibody reaction.

As set forth above, the simplified assays based on agglutination reactions are capable of detecting the presence of a substance, but are unsuitable for quantitative analyses wherein the amount of the substance present is to be determined. On the other hand, the enzyme immunoassays, in spite of their drawbacks of a prolonged reaction time and a troublesome B/F separation, are capable of conducting a quantitative assay as well as a qualitative assay since the results of the enzyme immunoassays may be represented in qualitative or quantitative forms by either the presence/absence or the degree of color change, namely, color development of the reaction solution. Also, the results may be easily and accurately discerned by anyone. Owing to such an advantage, a number of investigations have been carried out to shorten their reaction time and to simplify the B/F separation. As a matter of fact, an enzyme immunoassay satisfactory for practical use is not yet developed.

Recently, an assay utilizing a nucleic acid hybridization is employed for the simplified assay to detect a particular DNA or RNA (only DNA may be hereinafter mentioned, but detection of an RNA is also intended to be included within the scope of the invention). The nucleic acid-hybridization assay is analogous to the immunoassay utilizing an antigen-antibody reaction, especially an enzyme immunoassay, in that the reaction mechanism is based on selectivity of the DNA probe to hybridize with the particular DNA. Accordingly, steps included in enzyme immunoassays are likewise required in the nucleic acid-hybridization assay, and conventional nucleic acid-hybridization assays also suffer from the drawbacks of a long reaction time and a troublesome B/F separation, which should be overcome.

To overcome such drawbacks, Japanese Patent Application Kokai No. 63-20063 and Japanese Patent Application 62-215992 propose reaction vessels having a dish-like configuration.

By using the dish-like reaction vessels of these patent applications, qualitative enzyme immunoassays may be carried out by a significantly simplified procedure. These reaction vessels, however, are still insufficient to make the best of the advantage of the enzyme immunoassays that they may be used for quantitative assays.

The enzyme immunoassay involves a plurality of steps including, for example, sample dispensing and addition of washing solution, solution of an enzyme-labelled antibody, chromogenic reagent and enzyme substrate. Accordingly, this assay is quite complicated and requires a prolonged period before an evaluation can be made. These drawbacks are yet to be overcome.

For simplifying such an assay capable of conducting a quantitative evaluation, it would be essential to simplify the steps of B/F separation and addition of sample and various reagents. In such respects, the above-mentioned dish-like reaction vessels are yet to be improved.

SUMMARY OF THE INVENTION

As set forth above, a highly sensitive simplified assay which may realize an accurate measurement by a convenient operation is not yet developed.

The reaction vessel of the present invention is developed in view of such a situation in the art.

Accordingly, it is an object of the present invention to provide a reaction vessel which is capable of conducting a highly sensitive assay with an accurate and simple B/F separation by simple sample and reagent adding operations.

Another object of the present invention is to provide a reaction vessel of a wide application including such an assay as enzyme immunoassays and assays using nucleic acid hybridization.

A further object of the present invention is to provide a reaction vessel which is capable of assaying multiple items at a time by a simple operation.

Accordingly, this invention is directed to a reaction vessel adapted for enzyme immunoassays and nucleic acid-hybridization assays which is capable of continuously carrying out a series of steps including antigen antibody or hybridization reaction, B/F separation, enzymatic reaction, and evaluation of the results in a relatively short period.

The reaction vessel of the instant invention is capable of carrying out ordinary assays without any additional apparatus. However, the reaction vessel may be combined with other automatic measuring apparatus for the purpose of continuously treating a number of samples or enabling a quantitative evaluation.

Accordingly, the present invention, which fulfills the above-described requirements, comprises a reaction vessel comprising a body structure having provided therein at least one reaction unit comprising a channel having at least one fluid inlet and at least one reagent-immobilized area in the downstream of all of the at least one fluid inlet. The channel is provided with a vent mechanism, and the reagent-immobilized area has a reagent fixedly immobilized thereto.

BRIEF DESCRIPTION OF THE DRAWINGS

FIGS. 17a, 17b and 17c are schematic top plan views of reagent-immobilized zones according to different embodiments of the present invention wherein a plurality of reagent-immobilized areas are arranged in different patterns.

DETAILED DESCRIPTION OF THE INVENTION

The present invention is hereinafter described in detail.

The reaction vessel of the present invention comprises at least one reaction unit. A reaction vessel with one reaction unit is first described by referring to drawings although a wide variety of embodiments are included within the scope of the invention.

Figure 1A:
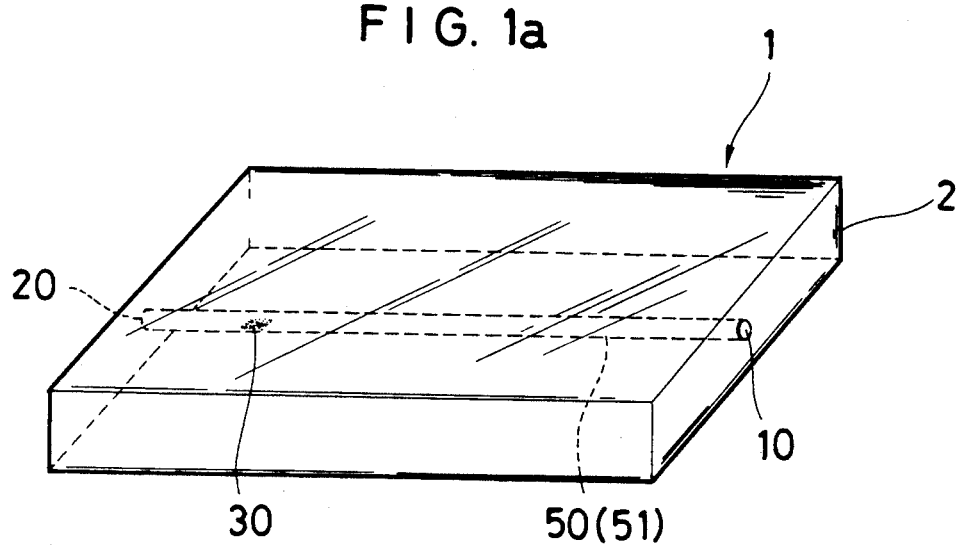
FIG. 1a is a perspective view of a reaction vessel according to an embodiment of the present invention.
Figure 1B:
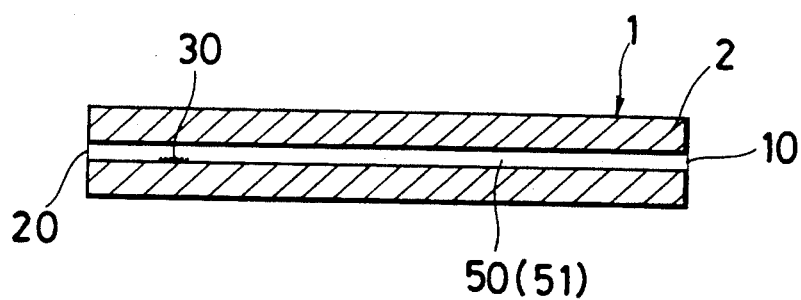
FIG. 1b is a cross-sectional view of the reaction vessel of FIG. 1a taken along a channel thereof.

FIG. 1a is a perspective view of a reaction vessel according to an embodiment of the present invention, and FIG. 1b is a cross-sectional view of the reaction vessel of FIG. 1a taken along a channel thereof.

Figure 2A:
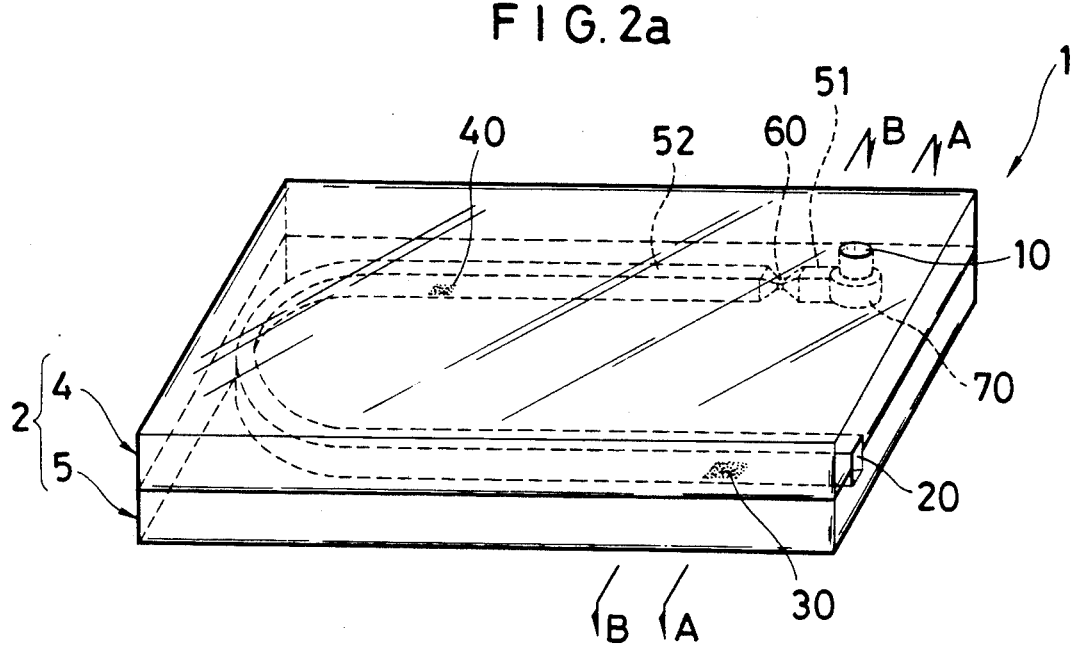
FIG. 2a is a perspective view of a reaction vessel according to another embodiment of the present invention.
Figure 2B:
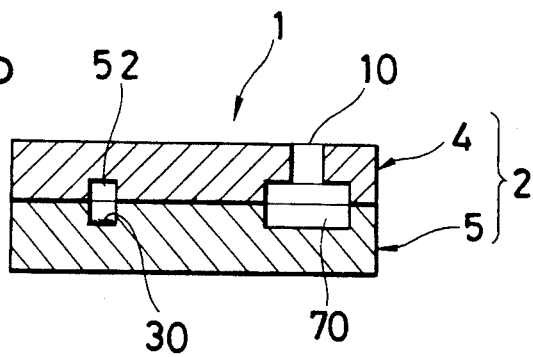
FIGS. 2b and 2c are cross-sectional views of the reaction vessel of FIG. 2a taken along lines A—A and B—B, respectively.
Figure 2C:
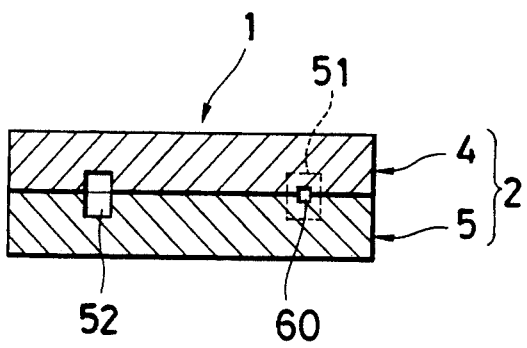

FIG. 2a is a perspective view of a reaction vessel according to another embodiment of the present invention, and FIGS. 2b and 2c are cross-sectional views of the reaction vessel of FIG. 2a taken along lines A—A and B—B, respectively.

Figure 3A:
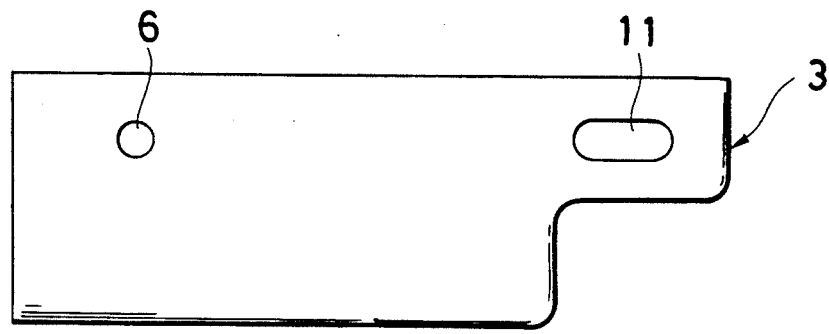
FIGS. 3a, 3b and 3c are top plan views of segments of a reaction vessel according to a further embodiment of the present invention.
Figure 3B:
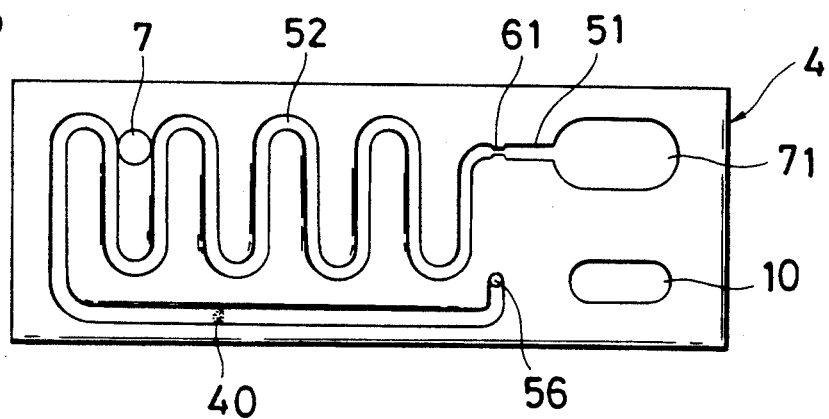
Figure 3C:
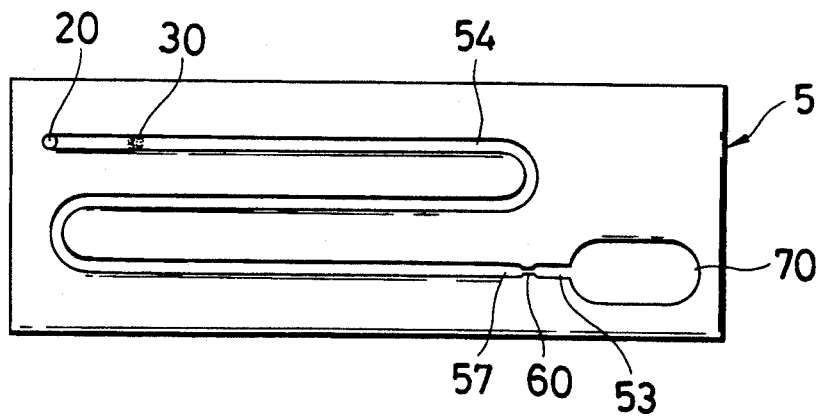
Figure 3D:
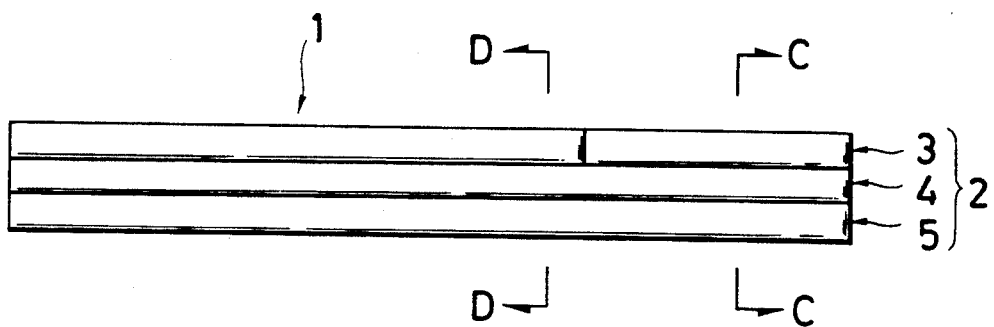
FIG. 3d is a side view of the reaction vessel comprising the segments of FIGS. 3a, 3b and 3c assembled together.
Figure 3E:
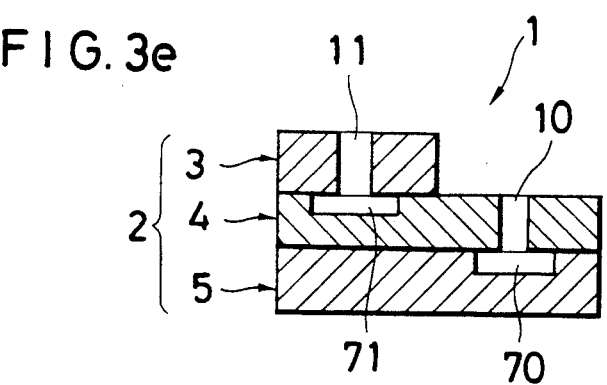
FIGS. 3e and 3f are cross-sectional views of the reaction vessel of FIG. 3d taken along lines C—C and D—D, respectively.
Figure 3F:
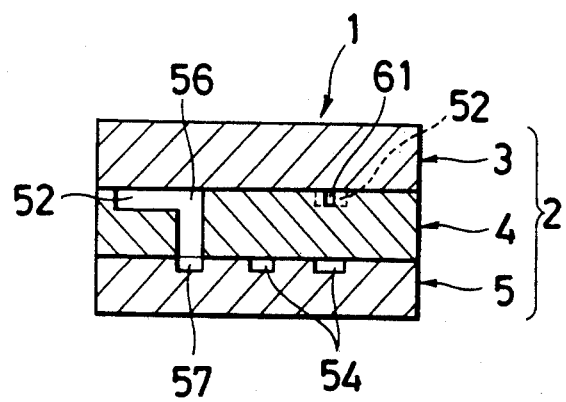

FIGS. 3a, 3b and 3c are top plan views of segments of a reaction vessel according to a further embodiment of the present invention, FIG. 3d is a side view of the reaction vessel comprising the segments of FIGS. 3a, 3b and 3c assembled together, and FIGS. 3e and 3f are cross-sectional views of the reaction vessel of FIG. 3d taken along lines C—C and D—D, respectively.

Figure 4:
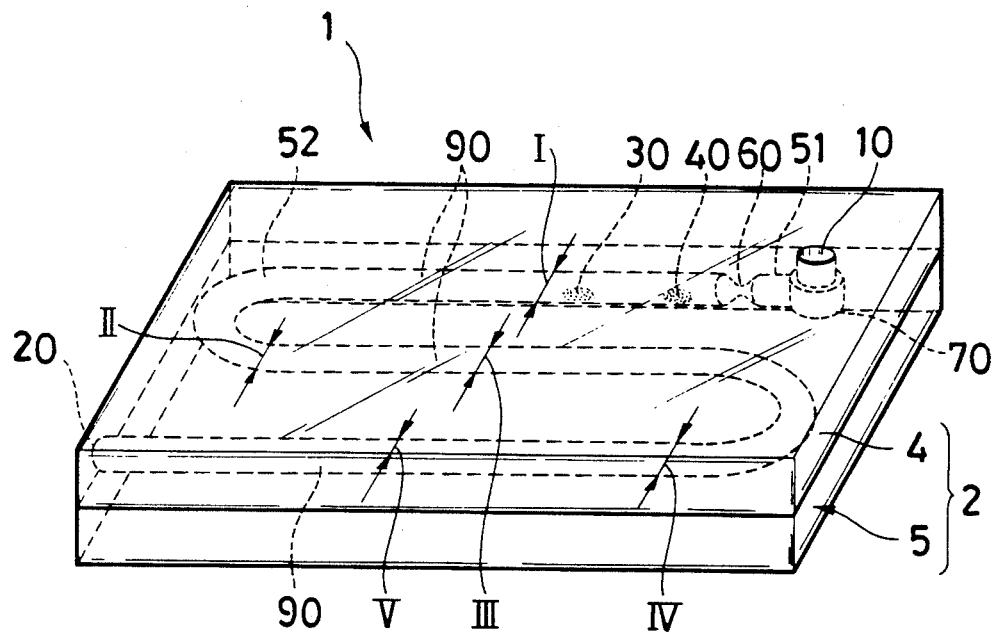
FIG. 4 is a perspective view of a reaction vessel according to a further embodiment of the present invention.

FIG. 4 is a perspective view of a reaction vessel according to a further embodiment of the present invention.

Figure 5:
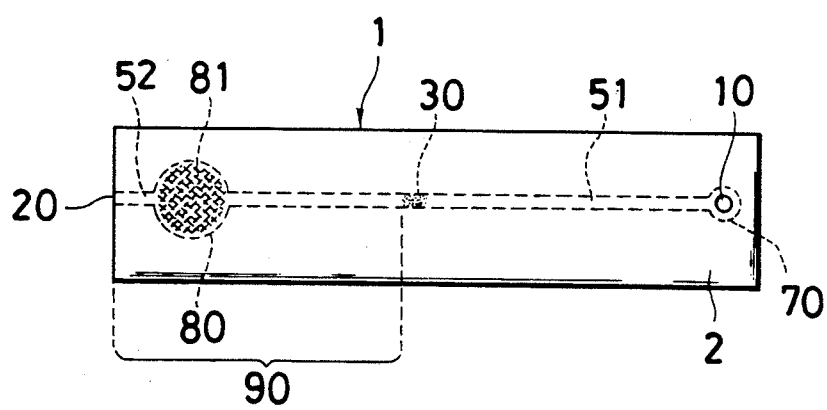
FIG. 5 is a top plan view of a reaction vessel according to a further embodiment of the present invention.

FIG. 5 is a top plan view of a reaction vessel according to a further embodiment of the present invention.

Figure 6A:
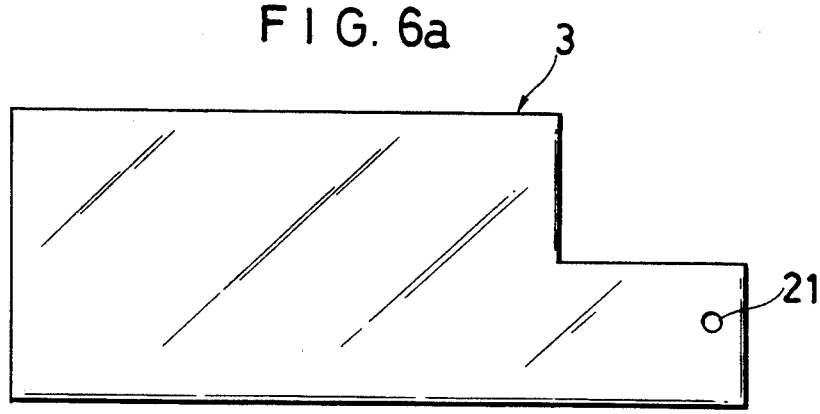
FIGS. 6a and 6b are top plan views of segments of a reaction vessel according to a further embodiment of the present invention.
Figure 6B:
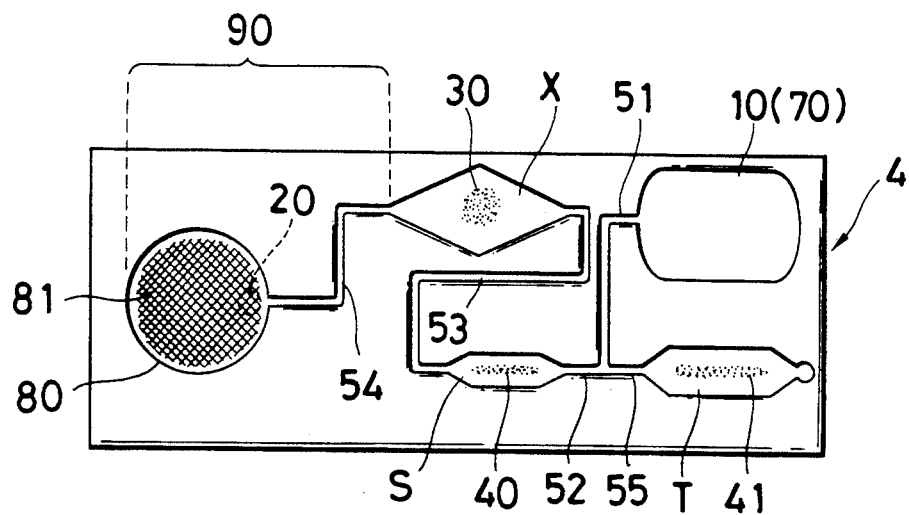
Figure 6C:
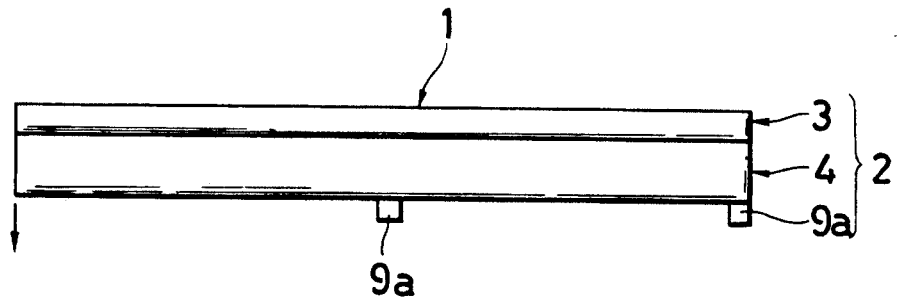
FIG. 6c is a side view of the reaction vessel comprising the segments of FIGS. 6a and 6b assembled together

FIGS. 6a and 6b are top plan views of segments of a reaction vessel according to a further embodiment of the present invention, and FIG. 6c is a side view of the reaction vessel comprising the segments of FIGS. 6a and 6b assembled together.

Figure 7A:
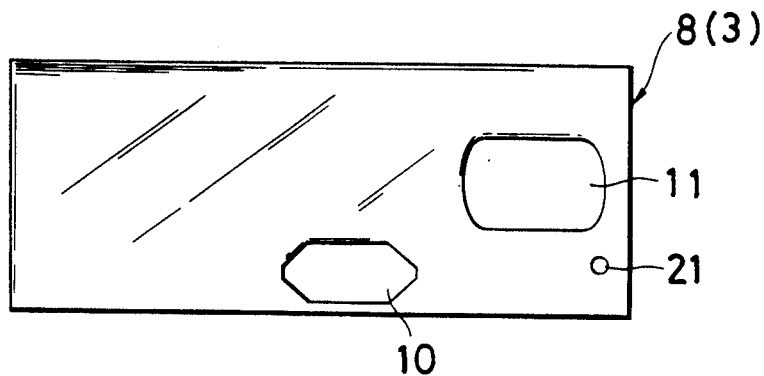
FIGS. 7a and 7b are top plan views of segments of a reaction vessel according to a further embodiment of the present invention.
Figure 7B:
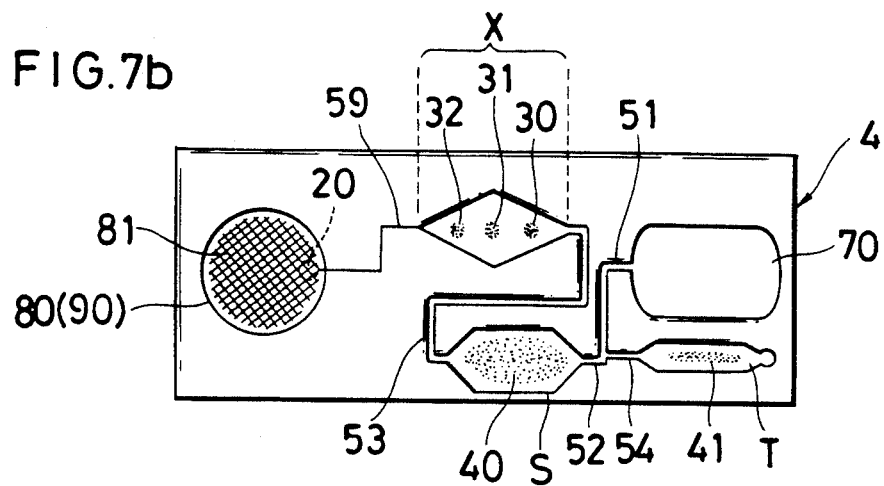
Figure 7C:
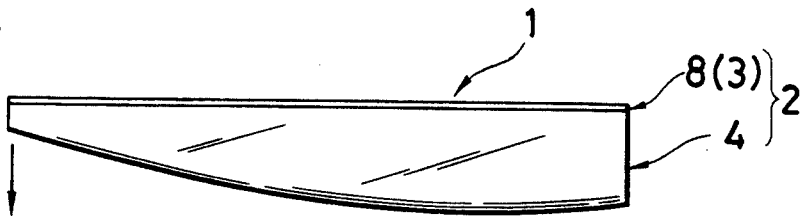
FIGS. 7c and 7d are side views of the reaction vessel comprising the segments of FIGS. 6a and 6b assembled together.
Figure 7D:
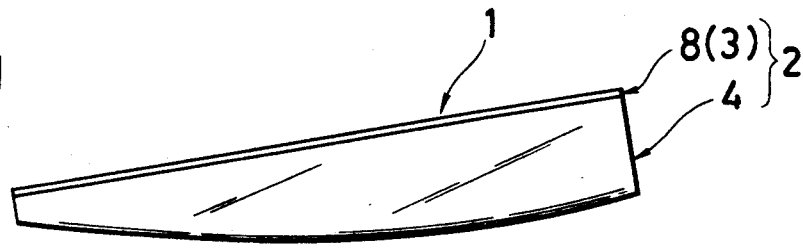

FIGS. 7a and 7b are top plan views of segments of a reaction vessel according to a further embodiment of the present invention, and FIGS. 7c and 7d are side views of the reaction vessel comprising the segments of FIGS. 6a and 6b assembled together.

Figure 8A:
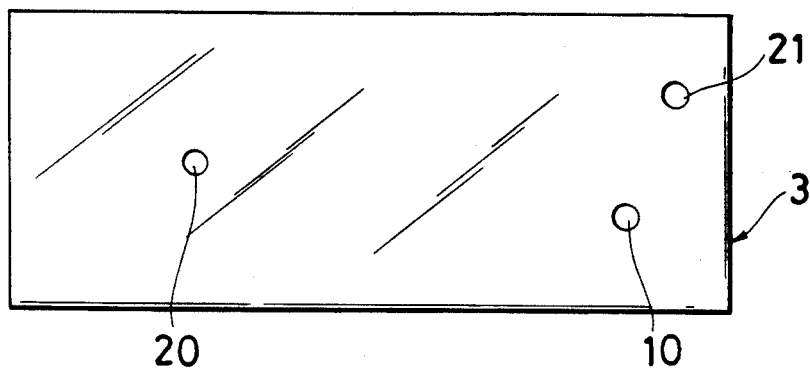
FIGS. 8a, 8b and 8c are top plan views of segments of a reaction vessel according to a further embodiment of the present invention.
Figure 8B:
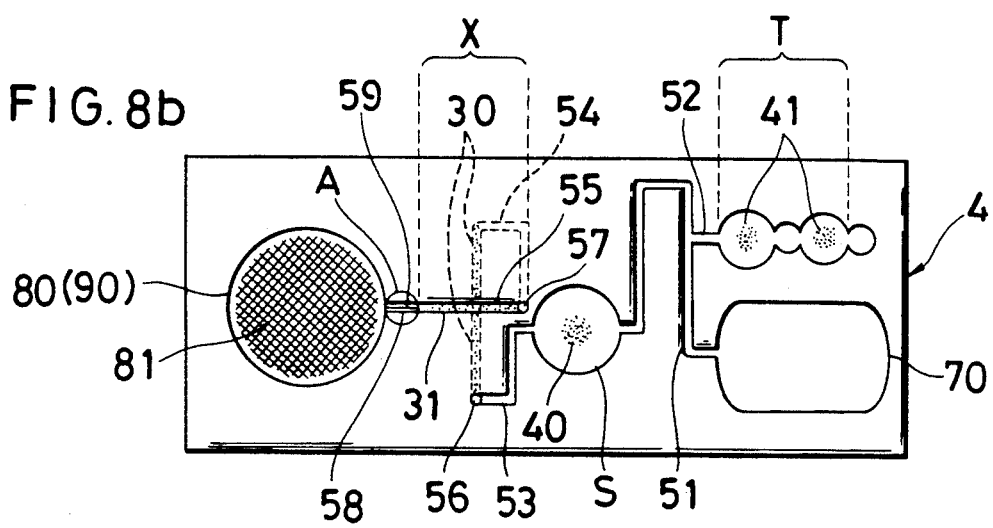
Figure 8C:
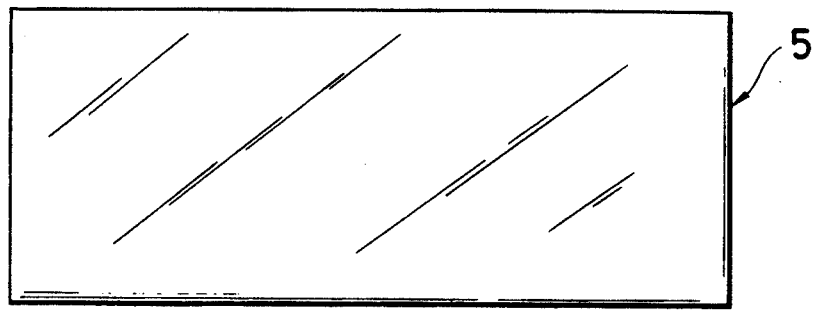
Figure 8D:
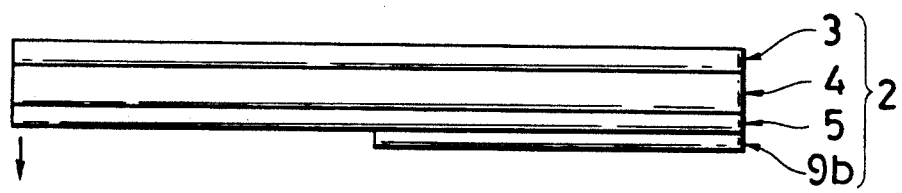
FIG. 8d is a side view of the reaction vessel comprising the segments of FIGS. 8a, 8b and 8c assembled together.
Figure 8E:
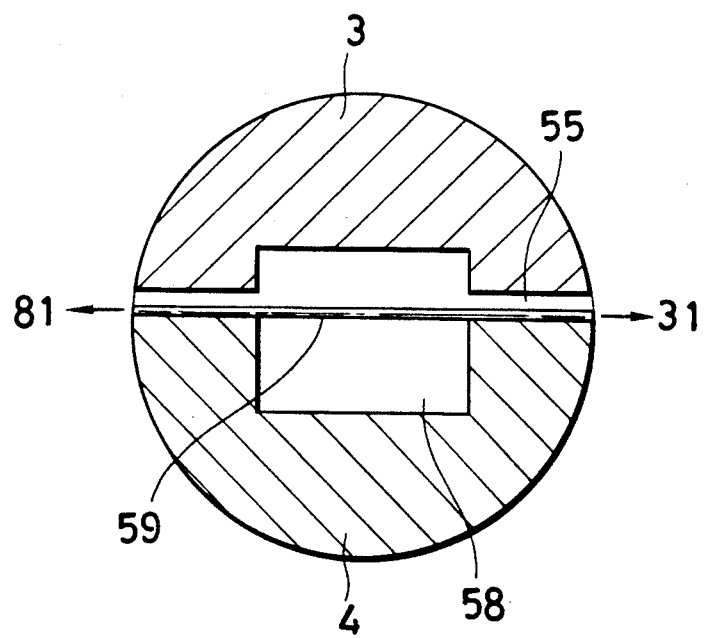
FIG. 8e is an enlarged cross-sectional view of the reaction vessel of FIG. 8d at part A of FIG. 8b.

FIGS. 8a, 8b and 8c are top plan views of segments of a reaction vessel according to a further embodiment of the present invention, FIG. 8d is a side view of the reaction vessel comprising the segments of FIGS. 8a, 8b and 8c assembled together and FIG. 8e is an enlarged cross-sectional view of the reaction vessel of FIG. 8d at apart A of FIG. 8b.

Figure 9A:
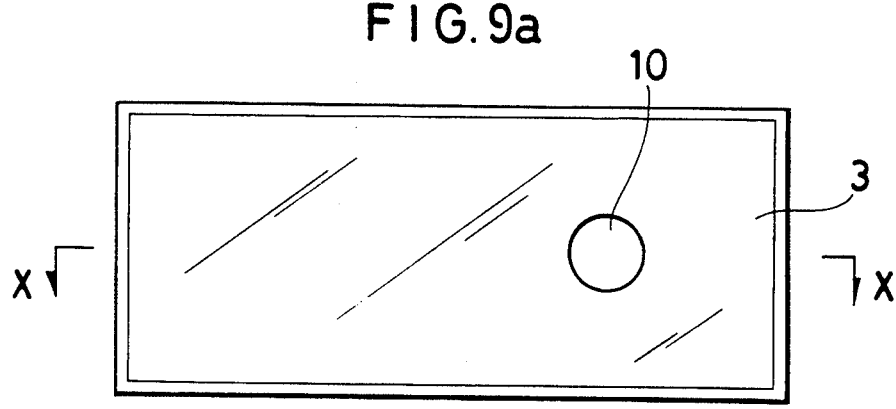
FIGS. 9a and 9b are top plan views of segments of a reaction vessel according to a further embodiment of the present invention.
Figure 9B:
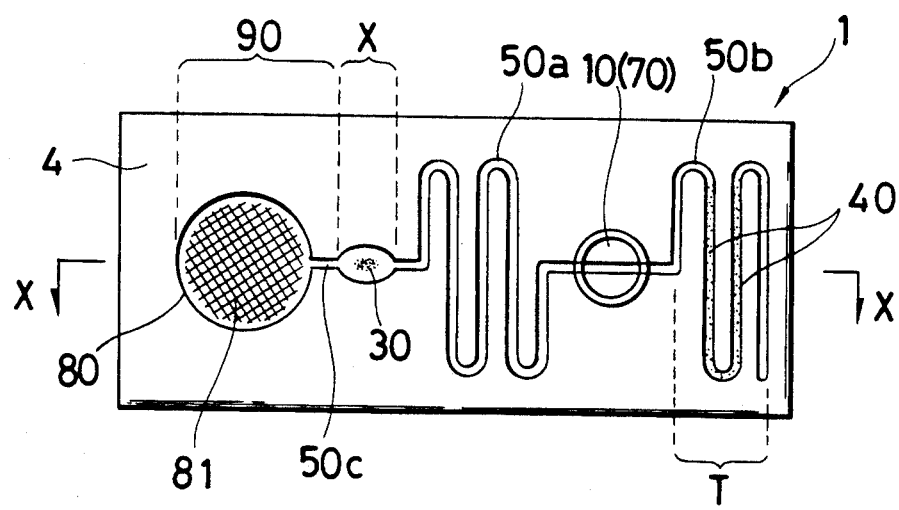
Figure 9C:
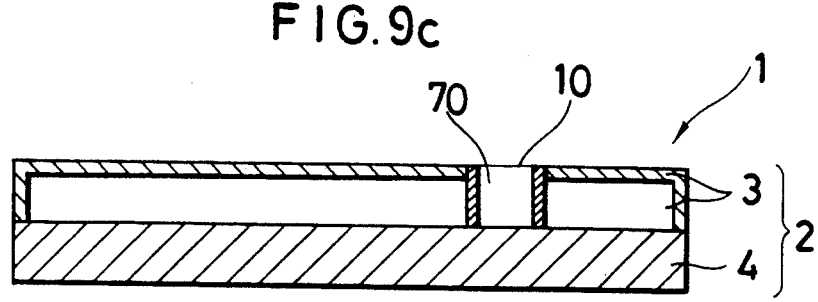
FIG. 9c is a side view of the reaction vessel of FIGS. 9a and 9b taken along lines X—X.

FIGS. 9a and 9b are top plan view of segments of a reaction vessel according to a further embodiment of the present invention. FIG. 9c is a side view of the reaction vessel of FIGS. 9a and 9b taken along lines X—X.

Figure 10:
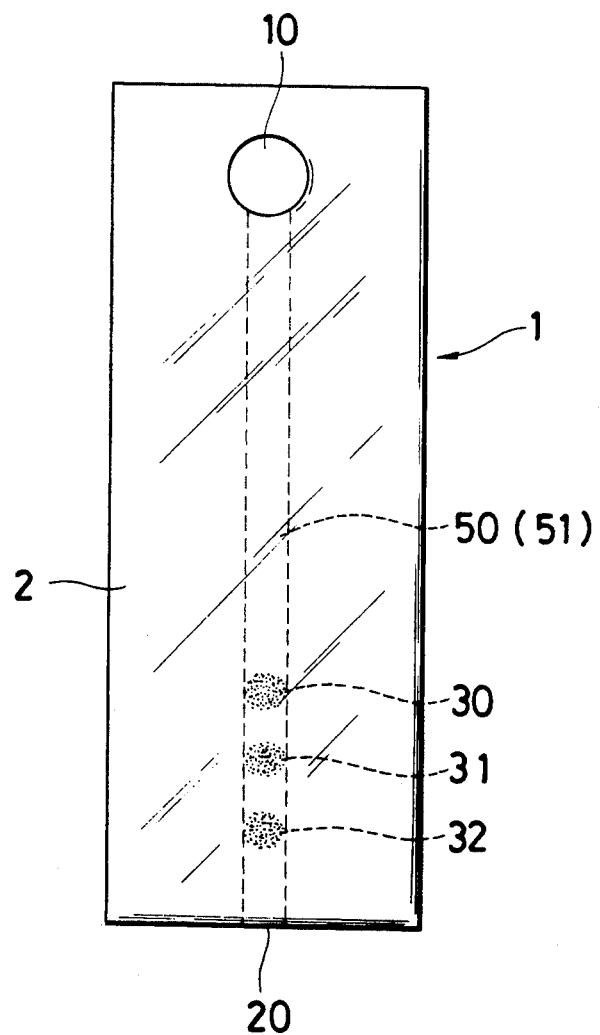
FIG. 10 is a top plan view of a reaction vessel according to a further embodiment of the present invention.
Figure 11:
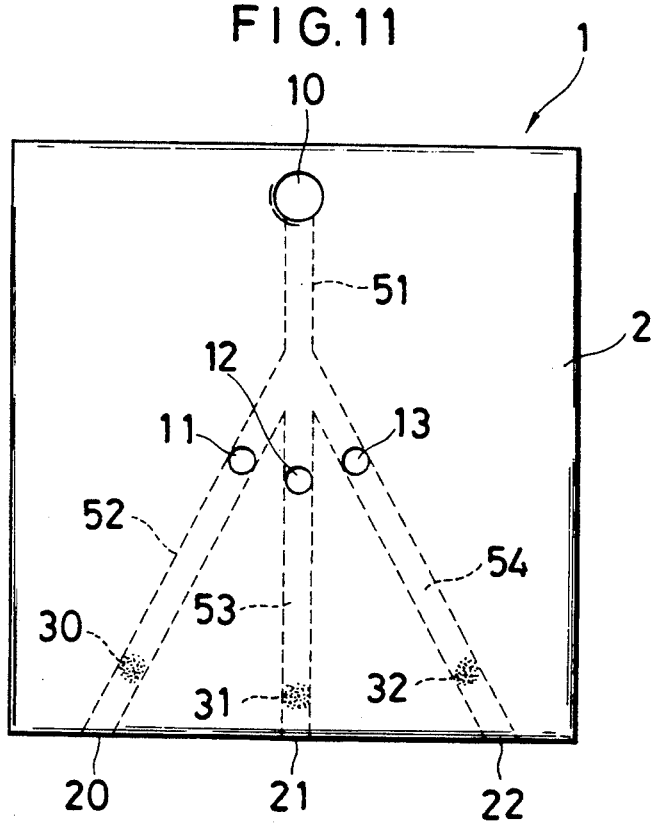
FIG. 11 is a top plan view of a reaction vessel according to a further embodiment of the present invention.
Figure 12:
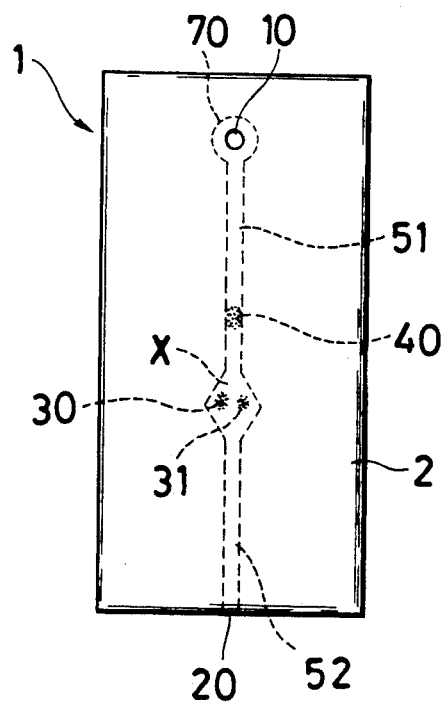
FIG. 12 is a top plan view of a reaction vessel according to a further embodiment of the present invention.

FIGS. 10, 11 and 12 are top plan views of reaction vessels according to further embodiments of the present invention.

The reaction unit of the present reaction vessel essentially comprises a body structure, a channel provided in the structure having at least one fluid inlet and at least one reagent-immobilized area in the channel in the downstream of all of the at least one fluid inlet. The channel has a vent mechanism, and the reagent-immobilized area has a reagent fixedly immobilized thereto.

Structure 2 may comprise one member as shown in FIG. 1a, two segments 4 and 5 as shown in FIGS. 2a and 4, three segments 3, 4 and 5 as shown in FIGS. 3d, 3e and 3f, or four or more segments.

Structure 2 may also comprise segments 4 and 5 and a pair of supports 9a as shown in FIG. 6c, segment 4 having a curved lower major surface and sheet-like segment 8 covering the upper major surface of segment 4 serving a lid for the channel as shown in FIG. 7c, or segments 3, 4 and 5 and plate 9b as shown in FIG. 8d.

The structure may preferably comprise at least two segments with the channel being provided in at least one of the channel for ease of providing the reagent-immobilized area and a reagent-attached area in the channel as will be described later. Alternatively, the structure may comprise a segment having the channel in an open state and a sheet-like lid covering the upper major surface of the segment with required parts of the channel being left open.

Structure 2 may also have a structure as shown in FIGS. 6c, 7c and 8d so that the reaction vessel will be inclined in the direction indicated by an arrow in each figure at the time of substantial completion of the reaction to indicate that the reaction has been substantially completed and the results are ready to be qualitatively or quantitatively evaluated.

The structure may comprise such materials as glass or plastic resins such as epoxy resins, polyacrylic resins, polyester resins, polystyrene resins and polyvinyl chloride resins. The material is either hydrophilic in itself or can be made hydrophilic by, for example, providing a frosted finish.

The uppermost segment of the structure 2 may be a sheet-like lid. This lid segment may comprise various materials as enumerated above for the structure 2, but may also comprise a metal such as aluminum. The sheet like segment may be bonded to other part of the structure 2 by heat-seal or with an adhesive layer disposed on one surface of the sheet-like segment.

Color of the structure is not particularly limited. When the results of the reaction are indicated by a color change, the structure may preferably be either totally transparent or comprise a transparent upper segment and white lower segment. When the results of the reaction are indicated by fluorescence, the structure may preferably be transparent.

The channel is provided in at least one segment of the structure. Various liquids such as samples, for example, urine and serum, washing solutions and reaction solutions as well as air passes through the channel. The channel has at least one fluid inlet. The channel is also in communication with a vent mechanism such as a ventilatory outlet.

The channel may have only one fluid inlet 10 as shown in FIGS. 1a, 2a, 4, 5, 6b, 8a, 9a, 10 and 12. The channel may also have two or more inlets 10 and 11 as shown in FIGS. 3a and 3b, and 7a.

When the channel is provided with a plurality of fluid inlets, a plurality of different liquids, for example, a sample and a reaction solution may be introduced into the fluid inlets either simultaneously or one after another in a predetermined order.

When the channel is provided with a plurality of fluid inlets, it is preferred to arrange fluid inlets 10 and 11 such that the fluid entering from the fluid inlet in the downstream will flow in substantially the same direction as the fluid entering from the most upstream fluid inlet as shown in, for example, FIGS. 3a through 3f.

Although the most upstream fluid inlet is provided in the upstream end of the channel in most cases, it is also possible to provide fluid inlet 10 in the midst of channel 50 as shown in FIG. 9b. However, in the embodiment of FIG. 9b, the fluid initially flowing upstream (toward right in FIG. 9b) will finally flow downstream.

The vent mechanism is typically a fluid outlet provided in the channel having a construction capable of ventilation.

Referring to FIGS. 1a, 2a, 4, 5 and 10, fluid outlet 20 comprises a downstream open end of the channel situated in the side surface of the structure. Referring to FIG. 3c, the channel is bent in its downstream end portion to form fluid outlet 20 opening at the lower major surface of the structure. In these cases, liquids including the sample and the reagents as well as gases such as air are discharged from fluid outlet 20.

Referring to FIGS. 6a, 6b, 7a, 7b and 8a, the channel is provided with two fluid outlets 20 and 21. The outlets may be situated in upper, side or lower surface of the structure. In these embodiments, as shown in top plan views of segments of FIGS. 6a, 6b, 7a, 7b, 8a and 8b, the channel is provided with fluid sump 90 and water-absorbent material 81 is accommodated in fluid sump 90 as will be described later. In such a case, the liquid within the channel rarely flows out of fluid outlet 20, and fluid outlet 20 is primarily used for ventilating purpose. Fluid outlet 21 is provided for the purpose of introducing the liquid into reagent-attached zone T including reagent-attached area 40 as will be described later. Fluid outlet 21 also serves as a vent.

Referring to FIG. 11, the channel is provided with three fluid outlets. In this embodiment, the channel is branched in midway to form branched channels (capillary channels 52, 53 and 54) and the downstream ends comprise fluid outlets 20, 21 and 22.

As described above, the fluid outlet may be designed so as to discharge the liquids introduced into the reaction vessel such as the sample and the reagents together with the gases in the channel. Alternatively, the fluid outlet may be so designed that the liquid introduced into the reaction vessel will be stagnated within the channel and only the gasses in the channel will be discharged therefrom.

The vent mechanism of the channel may not necessarily comprise such a fluid outlet.

Referring to FIGS. 9a, 9b and 9c, structure 2 comprises segment 4 having a channel in the upper surface and lid segment 3 bonded to segment 4 on 4 sides thereof to define a space between lid segment 3 and segment 4. When a liquid is introduced into the channel from fluid inlet 10, the gas or the air which was originally present in the interior of the channel will be transferred to the space defined between lid segment 3 and segment 4. The liquid will then be able to flow along the channel in spite of the absence of the fluid outlet.

Channel 50 of various configuration may be formed in structure 2 as described below.

Channel 50 may extend in various directions. Referring to FIGS. 1a and 1b, for example, channel 50 extends in a direction parallel to the main surface of structure 2. Referring to FIGS. 3d and 3f, the channel comprises sections each extending in a direction parallel or vertical to the main surface of structure 2. The channel may also have a slope running down from the fluid inlet to the fluid outlet or the fluid sump (not shown).

Channel 50 may have any desired path. The channel may have a straight path as shown, for example, in FIGS. 1a and 1b. The channel may also have a curved section as shown in FIGS. 2a, 3c and 4, or a winding section as shown in FIGS. 3b. The channel may also turn at abrupt right angle as shown in FIGS. 6b, 7b, 8b and 9b. The channel may also be branched as shown in FIG. 11.

Figure 13A:
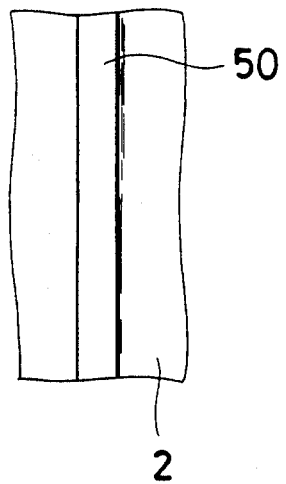
FIGS. 13a, 13b and 13c are fragmental top plan views of reaction vessels showing channels according to different embodiments of the present invention.
Figure 13B:
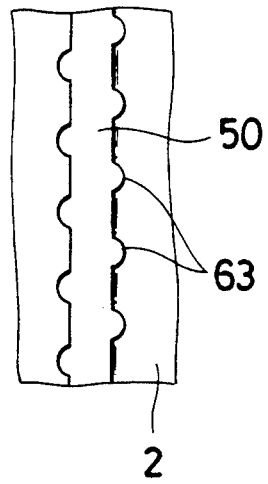
Figure 13C:
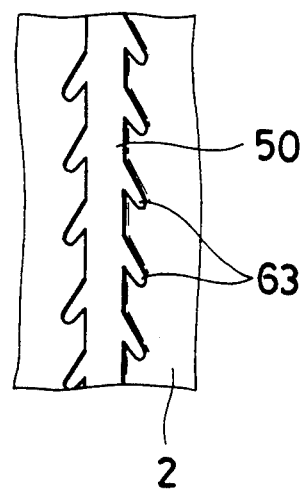

Channel 50 generally has a planar inside surface or inside wall as shown in FIG. 13a, although the channel is not limited to such a configuration and may have a dilated or widened portion 63 as shown in FIGS. 13b and 13c in top plan views.

Figure 14A:
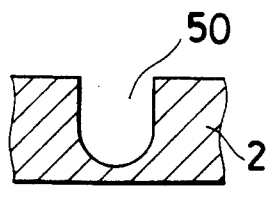
FIGS. 14a, 14b, 14c, 14d, 14e and 14f are fragmental cross-sectional views of reaction vessels showing channels according to different embodiments of the present invention.
Figure 14B:
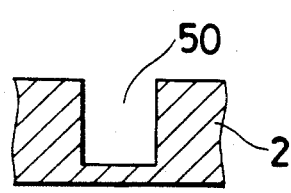
Figure 14C:
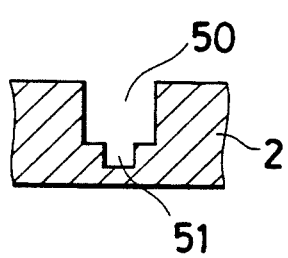
Figure 14D:
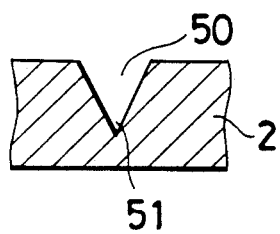
Figure 14E:
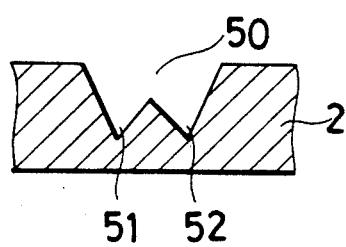

Channel 50 may have any desired cross section. Exemplary cross sections include a semioval or U-shape as shown in FIG. 14a, a rectangle as shown in FIG. 14b, a concave octagon as shown in FIG. 14c, a triangle or V-shape as shown in FIG. 14d and a concave pentagon or W-shape as shown in FIG. 14e, as well as circle and ellipsoid (not shown). In the embodiment of FIG. 14c, a narrowed bottom portion defined in the bottom of the channel forms capillary channel 51. In the embodiments of FIGS. 14d and 14e, acute angled bottom portion or portions define capillary channel 51 or capillary channels 51 and 52. In these embodiments, a smooth flow of the liquids along channel 50 is facilitated by capillary action. Alternatively, channel 50 may be formed as an elongated space having a width just sufficient for supporting the liquid therebetween as shown in FIG. 14f.

Figure 14F:
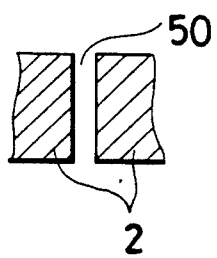

In the present invention, the term "capillary channel" does not necessarily designate a part of the channel in its cross section as in the case of FIGS. 14c, 14e and 14f. The term may also designate a predetermined length of the channel, wherein capillary action is induced.

Channel 50 may have an equal cross-sectional area throughout its length as in the case of FIGS. 1a and 1b. In such a case, the entire channel 50 comprises capillary channel 51. Channel 50 may include throat 60 or throats 60 and 61 and fluid reservoir 70 or fluid reservoirs 70 and 71 in addition to capillary channels 51, 52, 53, 54 and 55 as shown in FIGS. 2a, 3b, 3c and 4. The channel may also include fluid reservoir 70, reagent attached zone S or zones S and T having reagent-attached area therein, reagent-immobilized zone X having reagent-immobilized area therein, and fluid sump 90 as shown in FIGS. 5, 6b, 7b and 12. The channel may also include a zone wherein a hydrophilic thread 59 is accommodated for allowing the fluid to flow therethrough as shown in FIGS. 7b and 8b.

In the present reaction vessel, fluid reservoir 70 is provided near the fluid inlet. The liquid introduced into the reaction vessel is temporarily pooled in fluid reservoir 70 to enable a smooth introduction of the fluid into the reaction vessel.

Fluid reservoir 70 may have any desired size in accordance with amount of the fluids introduced into the reaction vessel and total internal volume of the channel. In a reaction vessel having fluid sump 90 to accommodate all of the fluids introduced into the reaction vessel within structure 2, fluid reservoir 70 may have an internal volume to meet the equation:

$$\text{Internal volume of fluid reservoir 70} \times \text{Frequency of fluid introduction} < \text{Internal volume of fluid sump 90}$$

Fluid reservoir 70 may extend beyond the upper major surface of segment 4 wherein the channel is defined as shown in FIG. 9c for the purpose of increasing the internal volume.

The throat controls the flow rate of the liquids within the channel, and at the same time, prevents the counterflow of the liquids.

The flow rate of the liquid within the channel may be readily controlled by providing fluid reservoir 70 near fluid inlet 10 and throat 60 near fluid reservoir 70 as shown in FIGS. 2a and 4, or by further providing fluid reservoir 71 near fluid inlet 11 and throat 61 near fluid reservoir 71 as shown in FIGS. 3a, 3b and 3c in top plan views of each segment.

In the embodiment whose top plan views of segments are shown in FIGS. 3a, 3b and 3c, throat 60 also prevents the liquids introduced from fluid inlet 11 in the upstream end of the channel from being drawn into fluid reservoir 70, which is in communication with downstream fluid inlet 10.

Fluid sump 90 accommodates the sample solution and various reagent and washing solutions which have gone through the reaction. Therefore, fluid sump 90 is formed in the downstream of the reagent-immobilized area.

In the embodiment of FIG. 4, fluid sump 90 comprises the part of capillary channel 52 in the downstream of reagent-immobilized area 30.

In the embodiment of FIG. 5, fluid sump 90 again comprises the part of capillary channel 52 in the downstream of reagent-immobilized area 30. In this embodiment, however, the channel is dilated in its downstream end to define absorbent material-accommodating area 80 to thereby increase the internal volume of fluid sump 90, and water-absorbent material 81 is accommodated in area 80. In the embodiments shown in FIGS. 6b, 7b, 8b and 9b, fluid sump 90 also either partly or totally comprises absorbent material-accommodating area 80 wherein water-absorbent material 81 is accommodated.

Typical water-absorbent materials include filter paper, high polymers such as so-called water-absorbent polymers, and natural fibers such as cotton wadding. The water-absorbent material is accommodated in at least a part of fluid sump 90.

Preferable water-absorbent materials include a copolymer of polyvinyl alcohol and sodium acrylate and cellulose, whose volumes does not significantly increase upon absorption of water.

Water-absorbent material 81 may be accommodated within area 80 with or without fixedly securing the material to the area by a known process, for example, with an adhesive or by sealing.

The amount of water-absorbing material used may be determined in accordance with the volume of the liquids introduced into the reaction vessel. Preferably, all of the liquids introduced into the vessel is absorbed by the water-absorbing material.

Water-absorbent materials are generally gas-permeable. The gas-permeability, however, may drop with the increase in volume of the liquids retained in the material. Therefore, in a reaction vessel wherein the channel is confined by the lid segment 3 on its upper side, it would be preferable to provide the channel with an outlet 20 in the upstream and in the vicinity of absorbent material-accommodating area 80 so that the gas may be discharged through the outlet even after the absorption/retention of the liquids within the water-absorbent material as shown in FIGS. 6b, 7b and 8a.

Provision of fluid sump 90 is particularly preferred when there is a danger of the sample being infectious or a contaminant being included in the sample, since the outlet, when provided, will be used only for the vent purpose and it will be possible to complete all the reactions without the sequentially introduced liquids being discharged from the reaction vessel. Disposal of the reaction vessel may then be readily carried out. Accommodation of water-absorbent material 81 in at least a part of fluid sump 90 is still more preferable since the liquids such as the sample introduced into the reaction vessel would be reliably absorbed and retained within the water-absorbent material without being discharged from the reaction vessel Water-absorbent material 81 also fulfills another preferable function of drawing the liquids through the channel to facilitate a smooth flow of the liquids introduced into the reaction vessel from the fluid inlet.

When the channel comprises a narrow zone having a relatively small cross-sectional area, which may be either a capillary channel or a non-capillary channel, and a dilated zone having a larger cross-sectional area to allow for a large volume of liquids to be accommodated therein, which may function as reagent-attached zone S or T or reagent-immobilized zone X, it is preferable to join the narrow zone and the dilated zone such that the dilated zone is gradually widened at a predetermined acute angle with the width of the dilated zone being gradually increased as shown in FIGS. 6b and 7b. Such a configuration of the dilated zone is a significant factor for the liquids flowing through the narrow zone to be able to continuously wet the interior of the dilated zone. When the dilated zone is suddenly widened at a dull angle with the width of the dilated zone being sharply increased as in the case of FIG. 8b, the dilated zone may preferably have a sloped bottom surface declining downwards from the upstream end to the downstream end. The liquids flowing through the narrow zone will then be able to continuously flow through the dilated zone with the help of gravity to wet the interior of the dilated zone.

In the embodiment wherein the channel includes a zone wherein hydrophilic thread 59 is accommodated for allowing the liquids to flow therethrough (FIGS. 7b and 8b), flow rate of the liquids flowing through the channel may be adjusted or controlled by the thread to any desired value.

In the reaction vessel of the present invention, flow rate of the liquids flowing through the channel is closely related to the precision of the reaction. More illustratively, in the case of an enzyme immunoassay, a high reaction accuracy may be realized by adjusting the flow rate to the lowest of the following:

(i) a flow rate suitable for completing the immunoreaction;

(ii) a flow rate suitable for completing the B/F separation; and (iii) a flow rate suitable for the color-developed substrate to be stably deposited on a predetermined position in the channel.

The flow rate of the liquids flowing through the channel is generally controlled by selecting an appropriate material for structure 2 and adjusting the cross-sectional area of the channel. The adjustment of the cross-sectional area may require a precise working or finishing of the channel involving a technical difficulty, and may result in an increased cost. When a thread is accommodated in a part of the channel for allowing the liquid to flow therethrough, the flow rate may be readily and precisely controlled by adequately selecting the type and the thickness of the thread. In particular, the flow rate of the liquids throughout the channel may be controlled by providing the hydrophilic thread in the immediate upstream of the fluid sump.

It is to be noted that the channel may be interrupted with the hydrophilic thread being stretched across the interruption as long as the liquids can flow through the hydrophilic thread at the interruption of the channel In turn, when the hydrophilic thread is accommodated in the channel, the part of the channel accommodating the hydrophilic thread does not necessarily require a precise working or finishing, and therefore, there will be induced no technical or economical problem.

Referring to FIGS. 8b and 8e, hollow chamber 58 is defined in the channel, and hydrophilic thread 59 is accommodated in the channel between reagent-immobilized area 31 and water-absorbent material 81 with hydrophilic thread 59 being stretched across hollow chamber 59. Referring to FIG. 8e, the liquids flowing through capillary channel 55 occupy the entire cross section of capillary channel 55 regardless of the hydrophilic thread 59 accommodated therein. In hollow chamber 58, the liquids flow only through hydrophilic thread 59 whose cross-sectional area is smaller than capillary channel 55. A full control of the flow rate is thus enabled to provide a necessary and sufficient time for the reactions to take place.

The hydrophilic thread may typically comprise a yarn, a paper or a fabric. The cross-sectional area of the hydrophilic thread may be suitably selected depending on the time required for completing the reactions. In the case of an immunoreaction, for example, the hydrophilic thread may have a circular cross section with a diameter of from about 0.2 to 1 mm.

The configuration of the channel has been described in the foregoing. The fabrication of the channel will be described in the following.

When channel 50 is defined in structure 2 comprising only one member as in the case of FIG. 1a, the channel may be formed by such means as boring. When the channel is defined in structure 2 comprising two segments 4 and 5 each having a part of the channel defined in its surface as in the case of FIG. 2a, each segment may be molded by preparing a mold corresponding to the shape of each of segments 4 and 5, introducing a resin material into the mold, curing the resin material, and knocking the molded segment out of the mold, and the molded segments may be assembled to define the channel therebetween. In the embodiment of FIG. 7c wherein structure 2 comprises segment 4 having a channel defined in its surface and a sheet-like lid segment 3, the channel may be formed by molding segment 4 and assembling segment 4 with sheet segment 3 so that the channel defined in the upper surface of segment 4 is covered by the lower surface of sheet segment 3. It is to be noted that the channel may be formed by such means as boring even when the structure 2 comprises two or more segments.

The segments are preferably bonded to each other with an adhesive.

When structure 2 comprises a plurality of segments, for example, segments 4 and 5, or segments 3, 4 and 5, adjacent segments may not necessarily contact with each other on their entire adjacent surfaces other than the portion of the channel.

Figure 15:
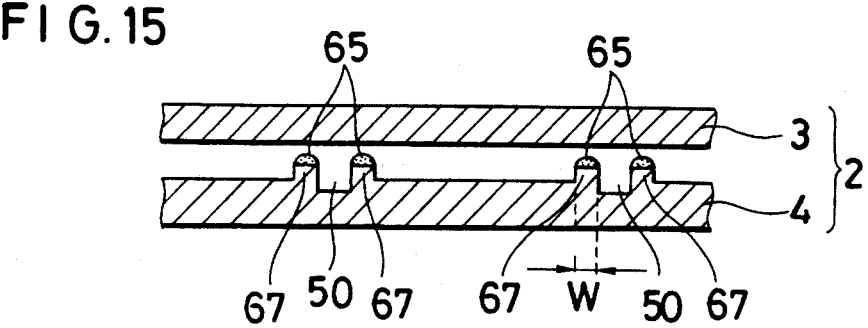
FIG. 15 is a partial cross-sectional view of a reaction vessel according to an embodiment of the present invention illustrating a process for fabricating a channel.

FIG. 15 is a partial cross sectional view of a reaction vessel according to one embodiment of the invention wherein the channel is defined by a pair of partitions 67 between adjacent segments. In this embodiment, a pair of partitions 67 are provided on the upper surface of segment 4 to define channel 50 therebetween, and segment 3 is bonded to segment 4 with adhesive 65. Therefore, adjacent segments 3 and 4 are in contact with each other only along partitions 67.

Partition 67 may preferably have a small width W for the purpose of a sufficient and uniform application of adhesive 65 along partition 67.

The adjacent segments may not necessarily be adhered to each other along a pair of partitions 67 as in the case of FIG. 15. In the reaction vessel of FIG. 9a, 9b and 9c, segments 3 and 4 are adhered to each other only along four sides.

Alternatively, the channel may be defined by extruding an adhesive to form a partition between two adjacent plate-like segments.

Figure 16A:
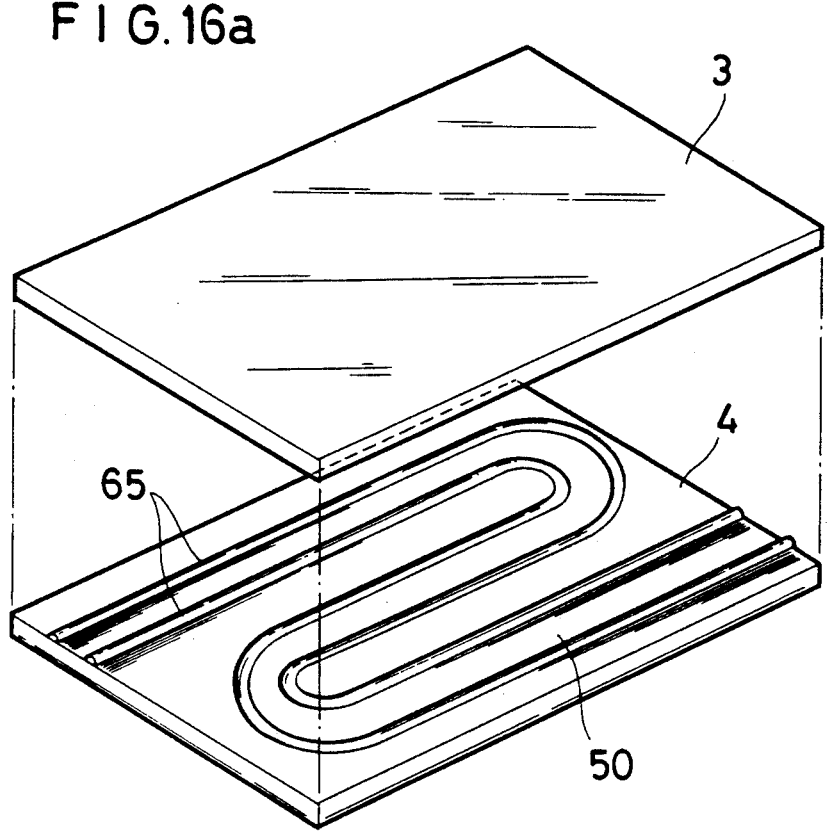
FIG. 16a is an exploded perspective view of a reaction vessel according to an embodiment of the present invention illustrating a process for fabricating a channel.
Figure 16B:
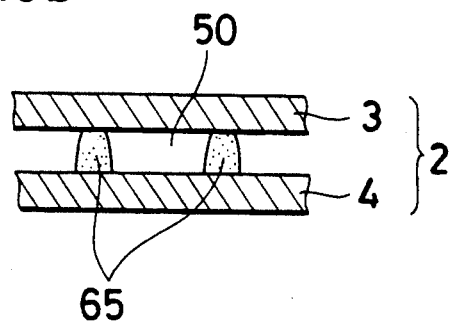
FIG. 16b is a partial cross sectional view of the reaction vessel depicted in FIG. 16a taken across a channel thereof.

FIGS. 16a and 16b, which are an exploded perspective view and a partial cross sectional view of the reaction vessel, are presented for illustrating such a process wherein the channel is defined between two segments 3 and 4 by extruding adhesive 65 to form a pair of partitions.

In this process, a sufficient amount of adhesive 65 is applied on segment 4 to form a pair of partitions along the path of channel 50 to define channel 50 therebetween. A spacer (not shown) having a height identical with that of channel 50 is placed between segments 3 and 4 before pressing segment 3 against segment 4 and curing adhesive 65. A reaction vessel having channel 50 defined with a pair of partitions comprising cured adhesive 65 is thereby fabricated.

The adhesive used for bonding the segments together may preferably be an adhesive of room temperature-curing type which has an appropriate viscosity and which does not undergo contraction upon curing. The adhesive may preferably have a low viscosity when it is applied to a large area, and a relatively high viscosity when it is applied to a small area. In the case of FIGS. 16a and 16b wherein the adhesive is extruded to define the channel, the adhesive should have shape-retaining properties. Typical adhesives include epoxy adhesive, vinyl acetate adhesive, synthetic rubber adhesive and cyanoacrylate adhesive.

It is to be noted that the step of bonding the segments together with the adhesive, or forming the channel with the adhesive may preferably comprise the last step of fabrication of the present reaction vessel.

When structure 2 is prepared from a non-hydrophilic material, it is required to make the surface of the segments hydrophilic at least along a part of the channel so that the liquids introduced into the reaction vessel can wet the interior of the channel to smoothly flow along the channel.

The process of preparing a hydrophilic surface is not limited to any particular process. The channel may be prepared from a material having a hydrophilic radical introduced on its surface. The channel surface may be subjected to a surface-roughening treatment such as blast finishing, plasma treatment, laser treatment and frost finishing. Alternatively, the channel surface may be coated with a hydrophilic substance such as an antistatic, for example, cationic surfactant or a protein.

The material used to make the channel surface hydrophilic may be a copolymer of methyl (meth)acrylate and (meth)acryl sulfate when structure 2 comprises a (meth)acrylic resin, and a styrene copolymer when structure 2 comprises a styrene resin.

When structure 2 comprises three or more segments, and the channel is defined between two adjacent segments the channel defined between two adjacent segments is connected to the channel defined between another two adjacent segments. Referring to FIGS. 3a, 3b, 3c, 3d, 3e and 3f, capillary channel 52 defined in the upper surface of segment 4 is connected to capillary channel 54 defined in the upper surface of segment 5 by a vertical channel 56 (57). Such a construction may allow for a relatively long channel to be formed in a relatively small structure 2.

When hydrophilic thread 59 is accommodated in a portion of the channel as in the case of FIGS. 7a, 7b and 7c, and FIGS. 8a, 8b, 8c, 8d and 8e, hydrophilic thread 59 may be fixed onto the channel at opposite ends and corners of the thread with an adhesive by any conventional method.

The reaction unit of the present reaction vessel has at least one reagent-immobilized area in the above-described channel.

The reagent-immobilized area is prepared by immobilizing a substance or a reagent which specifically binds to the substance to be detected onto the reagent-immobilizing area defined in the channel. The final reaction in a series of reactions which take place in the present reaction vessel is promoted in this area, and therefore, the results are evaluated in this area to determine the presence/absence or the quantity of the substance to be detected through observation in the case of a qualitative assay or measurement in the case of a quantitative assay.

The reagent which is immobilized onto the reagent-immobilizing area may typically be an antibody, an antigen, a hapten or a derivative thereof when the assay is based on an immunoreaction, and DNA or RNA when the assay is based on a nucleic acid-hybridization reaction. Other substances such as a lectine, a receptor and a ligand may also be used as the reagent so long as they specifically react with the substance to be assayed.

The reagent-immobilizing area is defined in the channel in the downstream of all of the at least one fluid inlet although the channel may extend to any desired length in the downstream of the reagent-immobilizing area. In an embodiment wherein the fluid introduced into the reaction vessel is discharged from the fluid outlet, the reagent-immobilized area is defined in the vicinity of the downstream end of the channel. In an embodiment wherein the fluid introduced into the channel is not discharged from structure 2, the reagent-immobilizing area is defined in a relatively upstream portion of the channel so that the fluid sump may be defined in its downstream.

The reagent-immobilizing area may have a non-limited configuration, for example, quadrilateral, circle, ellipsoid and hexagon.

As described above, the presence or the quantity of the substance to be assayed is determined in the reagent-immobilized area. In an embodiment wherein the channel is defined in two or more planes as in the case of FIGS. 3a through 3c and 8a through 8c, the results may be determined at a higher precision with either naked eye or optical equipments when reagent-immobilizing area 30 does not overlap with the channel in other plane.

When the results of the assay are indicated by a color development, a detection or measurement at a higher precision may be attained by fabricating portions 6 and 7 of segments 3 and 4 respectively corresponding to reagent-immobilized area 30 from a non colored, transparent material as in the case of FIGS. 3a, 3b and 3c.

When the results of the assay are to be determined with a transmitted light in such a reaction vessel, segment 5, wherein reagent-immobilizing zone 30 is defined, may also be fabricated from a non-colored, transparent material for evaluating the results at a high precision.

The reagent-immobilizing area may be defined in the channel without dilating the channel. Alternatively, the channel may be partly dilated to define a reagent-immobilizing zone to include either one reagent-immobilizing area or two or more reagent-immobilizing areas. The number of the reagent-immobilizing zone provided in the channel is not limited to one, and the channel may be provided with a plurality of reagent-immobilizing zones.

When a plurality of reagent-immobilizing areas are defined in the channel, an easy evaluation of the assay results at a high precision or a simultaneous multi-item assay may be enabled by arranging the reagent-immobilizing areas in an appropriate pattern.

Various embodiments wherein a plurality of reagent-immobilizing areas are defined in the channel are hereinafter described with reference to the drawings.

Referring to FIG. 12, two reagent-immobilizing areas 30 and 31 are provided in one reagent-immobilizing zone X. Referring to FIG. 7b, three reagent-immobilizing areas 30, 31 and 32 are provided in one reagent-immobilizing zone X. Referring to FIGS. 8b and 10, two reagent-immobilizing areas 30 and 31 or three reagent-immobilizing areas 30, 31 and 32 are provided in the capillary channel Referring to FIG. 11, branched capillary channels 52, 53 and 54 are provided with reagent-immobilizing areas 30, 31 and 32, respectively.

In the reaction vessels of FIGS. 7b, 8b, 10 and 12, the two or three types of reagents which are immobilized in the reagent-immobilizing areas are those which do not interfere or react with each other. When the reaction vessel is used for assaying a substance in a sample by an immunoreaction, the two or more reagents immobilized in the areas are antibodies, antigens or haptens which does not cross-react with each other.

On the other hand, the reagents which are immobilized in the reagent-immobilizing areas in the reaction vessel of FIG. 11 may interfere with each other.

When two or more reagents are immobilized in the reaction vessel as set forth above, one may be used for detection and others may be used for contrast purpose. Alternatively, different types of reagents may be immobilized for simultaneous multi-item assay. It is also possible to immobilize the same one reagent on two or more areas.

Referring to FIGS. 17a, 17b and 17c, a plurality of reagent-immobilizing areas are arranged in various patterns in reagent-immobilizing zone X.

In reagent-immobilizing zone X of FIG. 17a, reagent-immobilizing areas are arranged in fan shape. A reagent used for detection is immobilized in reagent-immobilizing area 30 in the center or pivot and a series of an authentic sample diluted to varying concentrations are immobilized in reagent-immobilizing areas 31 in position of arc. When the reaction vessel having reagent-immobilized areas arranged in such a pattern in reagent-immobilized zone X is used for simultaneously assaying the substance in the test sample to be assayed with an authentic sample diluted to varying levels, the result may be evaluated, for example, by comparing the degree of color development between the test sample and the diluted authentic samples to allow for an accurate semi-quantitative assay to be carried out. In the reaction vessel of FIG. 17b, the reagent-immobilizing areas are arranged in the pattern of "+". A reagent which reacts or binds to a substance which is always present in the sample but does not cross-react with the substance to be assayed is immobilized three reagent-immobilizing areas 31 arranged from left to right in the drawing. A reagent which selectively or specifically binds or reacts with the substance to be assayed is immobilized in the other two reagent-immobilizing areas 30. With such an arrangement, a "+" sign will be indicated within reagent-immobilized zone X when the substance to be assayed is present in the sample, since either of the above-described reactions will take place in all of the five reagent-immobilized areas and occurrence of such reactions are indicated by, for example, color development. When the substance to be assayed is absent in the sample, a "−" sign will be indicated in zone X since the reaction will take place only in the three reagent immobilized areas 31 of FIG. 17b. An easy evaluation of the results may thereby facilitated.

Reagent-immobilizing zone X in the reaction vessel of FIG. 8b also has reagent-immobilizing areas 30 and 31 arranged in the pattern of "+". When a reagent which reacts or binds to a substance which is always present in the sample but does not cross-react with the substance to be assayed is immobilized reagent-immobilizing area 31 arranged from left to right in the drawing and a reagent which selectively or specifically binds or reacts with the substance to be assayed is immobilized in reagent-immobilizing area 30 arranged from top to bottom in the drawing, a "+" sign will be indicated within reagent-immobilized zone X when the substance to be assayed is present in the sample while a "−" sign will be indicated within zone X when the substance to be assayed is absent in the sample.

Reagent immobilizing zone X of FIG. 17c has four reagent-immobilizing areas 32 in addition to the five reagent-immobilizing areas 31 and 32 which is similar to those illustrated in FIG. 17b. In the four additional reagent-immobilizing areas 32 of FIG. 17c, there is preferably immobilized a reagent which undergoes a reaction to give such an indication as a color development when a mistake is made in the operation such as an insufficient washing.

As set forth above, the provision of two or more reagent-immobilized areas in the channel may allow for a simultaneous multi-item assay or a simultaneous assay of the substance in the sample to be detected and the contrast substance to be carried out in the reaction vessel.

The immobilization of the reagent onto the capillary channel or the reagent-immobilizing zone may be carried out by any conventional method so long as the reagent is not removed through ordinary operation. The reagent may be immobilized either through a chemical binding or a physical adsorption such as an adsorption at an elevated temperature.

The reagent-immobilizing zone may have any desired size depending on the size of other part of the channel. The reagent-immobilizing zone having a rectangular shape in plan view may typically have a width or length in the range of from 10 to 15 mm.

When the channel of the present reaction vessel as described above is further provided with a reagent-attached area in the upstream of the reagent-immobilized area, the frequency of dispensing various reaction solutions into the reaction vessel may be reduced to enable a simple operation.

The reagent-attached area has a reagent tentatively attached thereto to a degree such that the reagent attached onto the reagent-attached area will be removed when a liquid flows over this reagent-attached area. The reagent-attached area, therefore, may be provided by such a process as applying an aqueous solution of the reagent at an appropriate position of the channel followed by lyophilization to attach the reagent onto the area.

The reagent-attached area may be located at any desired place in the upstream of the reagent-immobilized area. For example, reagent-attached area 40 of the reaction vessel of FIGS. 3a, 3b, 3c, 3d, 3e and 3f is situated in capillary channel 52. The reagent-attached area 40 may be alternatively provided in fluid reservoir 71.

Reagent-attached area 40 may also be provided within the channel in the upstream of fluid inlet 10 as shown in FIG. 9b. With such an arrangement, the reagent attached in reagent-attached area 40 will reach reagent-immobilized area 30 after the substance in the sample to be assayed has fully reacted with the reagent immobilized in reagent-immobilized area 30.

Referring to FIGS. 6b, 7b and 8b, reagent-attached zones S and T each having a large inner volume are provided in the channel, and reagent-attached areas 40 and 41 are included in reagent-attached zones S and T, respectively. The number of the reagent-attached area included in one reagent-attached zone is not limited to one, and two reagent-attached areas 41 may be provided in reagent-attached zone T as in the case of FIG. 8b. When such a reaction vessel is used for an enzyme immunoassay of an antigen in the sample by sandwich method after attaching an enzyme-labelled antibody and a substrate for the enzyme in its reagent-attaching areas, the only operation required for completing all the necessary reactions would be introduction of the sample into the reaction vessel.

The reagent which is attached onto the reagent-attaching area is either a reagent which binds to the substance in the sample to be assayed or a reagent which binds to the reagent immobilized in the reagent-immobilized area. Exemplary such reagents include a labelled antigen, a labelled antibody, a labelled hapten, a labelled DNA, and when an enzyme is used for the label, a substrate for the enzyme label.

The provision of the reagent-attached zone having a cross-sectional area larger than that of the capillary channel is preferable in terms of fully promoting the reactions.

As described above, the reagent-immobilized area and the reagent-attached area are formed by immobilizing or attaching the predetermined reagent within the area. A more reliable contact or reaction between the substance in the sample to be assayed and the reagent immobilized or attached in the area may be facilitated by providing the reagent-immobilizing area or the reagent-attaching area with a recess and/or a group of protrusions and immobilizing or attaching the reagent within the recess and/or within the recess.

Figure 18A:
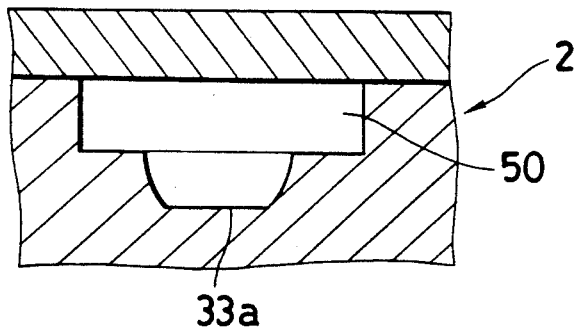
FIGS. 18a, 18b and 18c are partial schematic cross-sectional views of reaction vessels according to different embodiments of the invention taken across a channel at a reagent-immobilized area, wherein said reagent-immobilized area comprises a recess provided in the channel, a group of protrusions in the channel, and a group of protrusions provided within a recess in the channel, respectively.
Figure 18B:
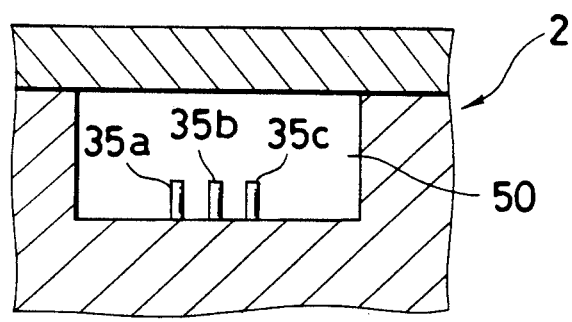
Figure 18C:
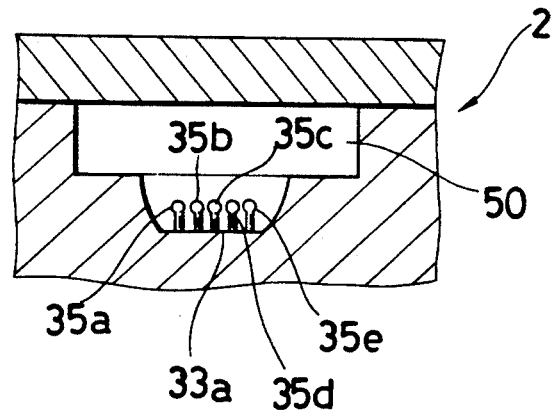

FIG. 18a is a cross-sectional view of structure 2 wherein recess 33a is formed in the bottom surface of channel 50. FIG. 18b is a cross-sectional view of structure 2 wherein a group of protrusions 35a, 35b and 35c are mounted on the bottom surface of channel 50. FIG. 18c is a cross-sectional view of structure 2 wherein recess 33a is formed in the bottom surface of channel 50 and a group of protrusions 35a through 35e are mounted on the bottom surface of recess 33a. Such a recess or a group of protrusions may be formed by any desired method known in the art, and they may be formed simultaneously with or subsequent to the formation of the channel.

When the recess is formed in the channel to immobilize the reagent therein, it is preferable to form reagent-immobilizing zone X to accommodate recesses 33a to 33i arranged in the pattern of fan shape or "+" as shown in the above-described FIGS. 17a, 17b and 17c.

When the reagent-immobilizing area is provided with groups of protrusions, it is also preferable to arrange them in the pattern of fan shape or "+".

Figure 19A:
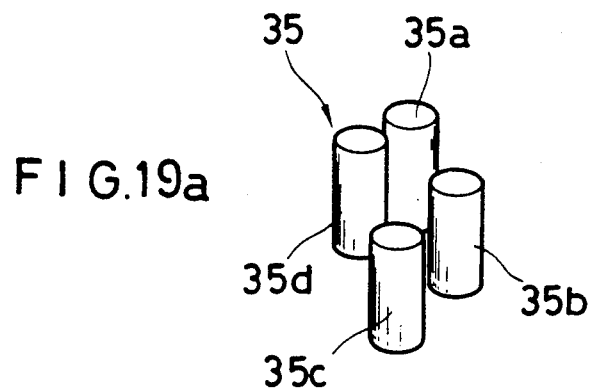
FIGS. 19a, 19b and 19c are schematic views of groups of protrusions according different embodiments of the present invention.
Figure 19B:
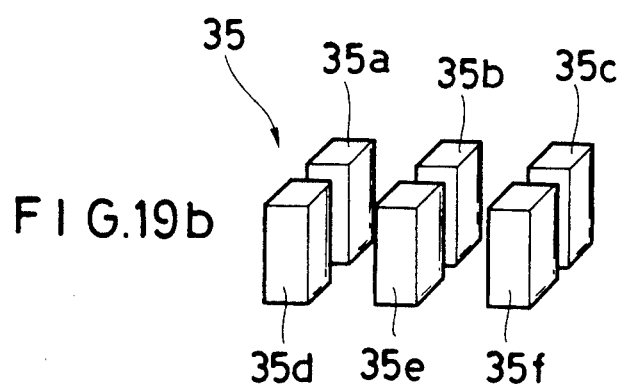
Figure 19C:
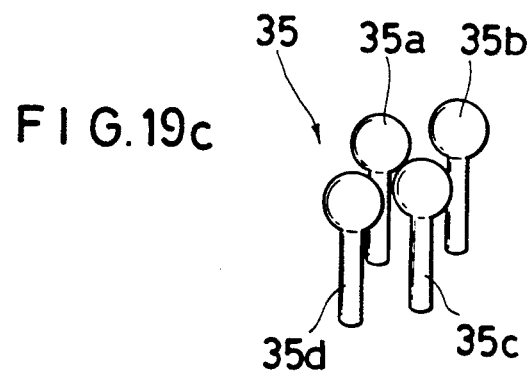

Individual protrusions 35a through 35f constituting the group of protrusions 35 may be a circular cylinder, a prism, or a circular cylinder with swollen head as shown in FIGS. 19a, 19b and 19c.

The protrusion may preferably have a cross-section with a diameter or a side in the range of about 0.3 μm to 1.0 mm.

The protrusion may have a height which suits its cross-sectional area. The height may preferably be in the range of about 0.5 to 2.0 mm.

The protrusions are spaced from each other such that the liquids are retained between the protrusions.

The liquids are believed to be retained between the protrusions through surface tension and capillary action. Therefore, the distance between the adjacent protrusions should be short enough to allow for the surface tension and the capillary action to be functioned. However, when the distance is too short, the liquids such as the sample and various reaction solutions may not smoothly get into the space between the protrusions, and the washing carried out for the B/F separation may be insufficient. A distance sufficient for avoiding such inconvenience is therefore required. Preferably, the distance between the protrusions is in the range of from 0.5 to 1.5 mm.

The provision of the recess and/or the group of protrusions results in an increased surface area to allow for a larger volume of reagent to be immobilized or attached in the area. The depth of the liquid retained in the reagent-immobilized area will also increase since the liquid is retained within the recess and/or between the protrusions. When the results are evaluated by a color development, the strength of the color is enhanced owing to the thus increased depth. Precision of the assay is thereby improved.

Figure 20:
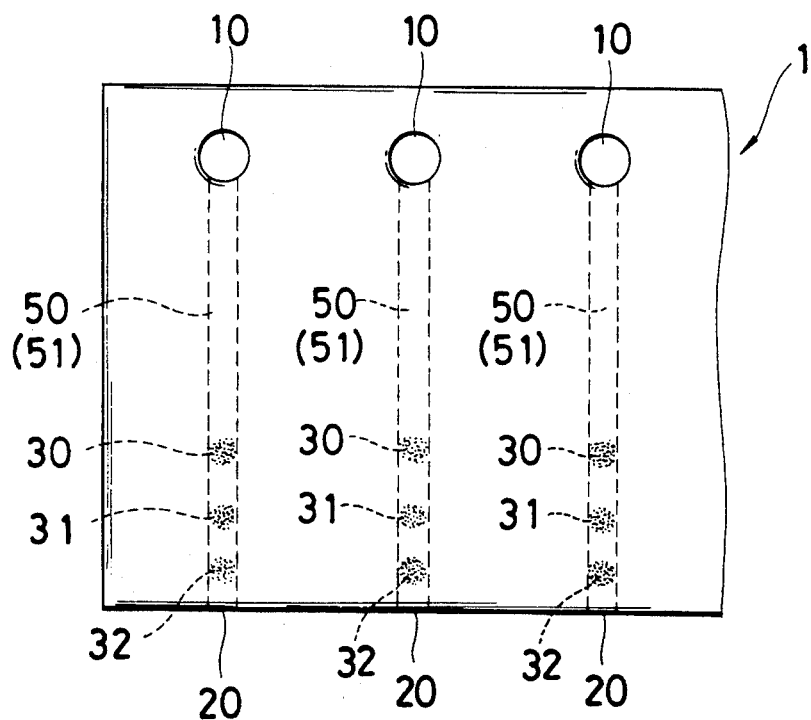
FIG. 20 is a partial top plan view of a reaction vessel according to a further embodiment of the present invention.
Figure 21:
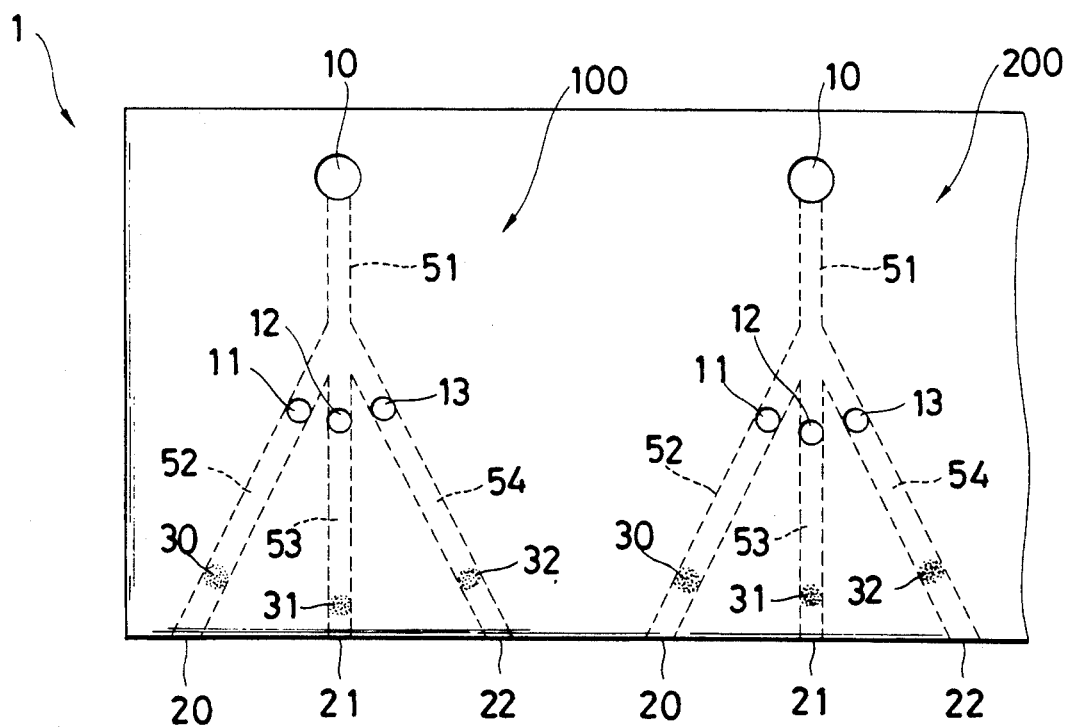
FIG. 21 is a partial top plan view of a reaction vessel according to a further embodiment of the present invention.

The reaction vessel of the present invention may also include two or more of the above-described reaction units arranged in rows. Exemplary such reaction vessels are shown in FIGS. 20 and 21 in partial top plan views.

By using such a reaction vessel having two or more reaction units arranged in rows, a plurality of samples or a sample together with a contrast or a standard solution may be simultaneously reacted under identical conditions.

When the reagent immobilized is altered from unit to unit, a larger number of items may be simultaneously assayed compared to the reaction vessels of FIGS. 10, 11 and 12.

The reaction vessel of the present invention has been heretofore described with regard to its construction. The movement of the liquids within the reaction vessel in the practical use is hereinafter described.

The movement or behavior of the liquids introduced into the reaction vessel of the present invention may be generally divided into five types.

According to the first type of the liquid movement, the liquids such as the sample which is sequentially introduced into the reaction vessel is discharged from the outlet once the channel is filled with the liquids. This is the case of the reaction vessel of, for example, FIGS. 1a and 2a.

The liquid movement of the second type is found in the reaction vessel of, for example, FIG. 4 wherein channel 50 has reagent-immobilized area 30 provided at a position upstream enough to define fluid sump 90 in its downstream.

The movement of the liquids in the reaction vessel of FIG. 4 is described below with regard to the case wherein the substance in the sample to be assayed is an antigen, reagent-immobilized area 30 has a monoclonal antibody against the substance to be assayed immobilized thereto, and reagent-attached area 40 has an enzyme-labelled monoclonal antibody attached thereto.

(1) The sample is introduced into the channel until the sample reaches position I indicated in FIG. 4.

(2) The washing solution is introduced into the channel until the sample reaches position II in FIG. 4.

(3) The substrate solution for the enzyme is introduced into the channel until the sample reaches position III in FIG. 4.

(4) The washing solution is introduced into the channel until the sample reaches position IV in FIG. 4.

(5) The chromogen solution is introduced into the channel until the sample reaches position V in FIG. 4.

As set forth above, the liquids sequentially introduced into the channel is retained within the reaction vessel without being discharged therefrom.

In the reaction vessel wherein water-absorbent material 81 is accommodated in at least a part of fluid sump 90 to define absorbent material-accommodated area 80 as in the case of FIG. 5, all of the liquids sequentially introduced into the channel is absorbed in water-absorbent material 81 and retained therein. The liquid movement is similar to the above-described liquid movement in reaction vessel of FIG. 4.

The liquid movement of the third type is found, for example, in the reaction vessels FIGS. 6b and 8b wherein the channel has one fluid inlet and the channel is branched The movement of the liquids in the reaction vessel of FIG. 6b is described below with regard to the case wherein the substance in the sample to be assayed is an antigen, reagent-immobilized area 30 in reagent-immobilized zone X has a monoclonal antibody against the antigen to be assayed immobilized thereto, reagent-attached area 40 in reagent-attached zone S has an enzyme-labelled monoclonal antibody attached thereto, and reagent-attached area 41 in reagent-attached zone T has a substrate for the enzyme attached thereto.

(1) The sample is introduced into the channel from fluid inlet 10 to fill fluid reservoir 70.

(2) The sample proceeds through capillary channels 51 and 52 into reagent-attached zone S and through channels 51 and 55 into reagent-attached zone T.

(3) Once capillary channel 55 and reagent-attached zone T are filled with the sample, the sample is drawn from fluid reservoir 70 through capillary channel 51 and capillary channel 52 to reagent-attached zone S, and further, through capillary channel 53 to reagent-immobilized zone X, and still further, through capillary channel 54 to absorbent-material-accommodated area 80.

(4) When fluid reservoir 70 and capillary channel 51 become empty, the sample filled in capillary channel 55 and reagent-attached zone T is drawn through capillary channel 52 to reagent-attached zone S, and further, through capillary channel 53 to reagent-immobilized zone X, and still further, through capillary channel 54 to absorbent material-accommodated area 80.

As set forth above, all the necessary reactions may be completed by simply introducing the sample into the channel since the channel is branched to enable for the different reagents to be attached to different positions of the channel in order to supply the suitable reagent in accordance with the order of the reactions.

The liquid movement of the fourth type is a variation of the above-described third type, and is found, for example, in the reaction vessel of FIG. 9b wherein the channel has reagent-attached area 40 in the upstream of fluid inlet 10. It is to be noted that no fluid outlet is particularly provided in the channel of the reaction vessel of this type since the channel is open on its upper surface as shown in FIG. 9c.

The movement of the liquids in the reaction vessel of this type is described below with regard to the case wherein the substance in the sample to be assayed is an antigen, reagent-immobilized area 30 in reagent-immobilized zone X has a monoclonal antibody against the antigen to be assayed immobilized thereto, and reagent-attached area 40 in reagent-attached zone T has a fluorescence-labelled monoclonal antibody attached thereto (1) The sample is introduced into the channel from fluid inlet 10 to fill fluid reservoir 70.

(2) The sample proceeds into channel 50a in the downstream of fluid reservoir 70 toward fluid sump 90. At the same time, the sample proceeds into channel 50b in the upstream of fluid reservoir 70 to fill reagent-attached zone T, whereupon the fluorescence-labelled monoclonal antibody dissolves into the sample solution.

(3) The sample drawn into channel 50a proceeds into reagent-immobilized X, and the antigen included in the sample is immobilized onto reagent-immobilized area 30. The sample further moves through channel 50c into absorbent-material-accommodated area 80.

(4) When fluid reservoir 70 becomes empty, the sample filled in channel 50b having the fluorescence-labelled monoclonal antibody dissolved therein is drawn through channel 50a to reagent-immobilized zone X, and further, through channel 50c to absorbent material-accommodated area 80.

As set forth above, the provision of reagent-attached zone T in the upstream of fluid inlet 10 results in an increased time interval between the arrival of the substance in the sample to be assayed and the arrival of the labelling reagent to reagent-immobilized zone X to facilitate a sufficient immobilization of the substance to be assayed onto reagent-immobilized zone X.

It is to be noted that a washing solution may optionally be introduced into the channel from fluid inlet 10 to fully remove the unreacted fluorescence-labelled monoclonal antibody from the reagent-immobilized zone.

The liquid movement of the fifth type is found in the reaction vessel wherein the channel has a plurality of fluid inlets as shown in FIGS. 3a, 3b and 3c and in FIGS. 7a and 7b in top plan views of segments of the reaction vessel.

In the reaction vessel whose top plan views of the segments are shown FIGS. 3a, 3b and 3c, the sample introduced into the channel from fluid inlet 10 fills fluid reservoir 70, and proceeds through capillary channel 60, throat 60 and capillary channel 54 to outlet 20. On the other hand, liquids including the buffer and reaction solutions introduced into the channel from fluid inlet 11 fill fluid reservoir 71 and proceeds through capillary channel 51, throat 61, capillary channel 52, communicating channel 56 (57) and capillary channel 54 to outlet 20. Therefore, the liquids introduced from fluid inlet 11 will reach reagent-immobilized area 30 after the sample solution introduced from fluid inlet 10 has gone through reagent-immobilized area 30.

In the reaction vessel whose top plan views of the segments are shown in FIGS. 7a and 7b, the sample introduced into the channel from fluid inlet 10 first goes through reagent-immobilized zone X, and thereafter, liquids such as the buffer and reaction solutions introduced into the channel from fluid inlet 11 goes through reagent-immobilized zone X.

The reaction vessel of FIG. 11 is also provided with a plurality of fluid inlets The reaction vessel of this type is useful in such a case wherein the samples or the reagents which react with each of the reagents immobilized in reagent-immobilized areas 30, 31 and 32 should be introduced separately from each other without mixing them together before the introduction.

The reaction vessel of FIG. 11 may be used in such a way that the sample introduced into the channel from fluid inlet 10 goes through reagent-immobilized areas 30, 31 and 32 before the reaction solutions introduced from fluid inlets 11, 12 and 13 go through reagent-immobilized areas 30, 31 and 32, respectively. Alternatively, it may be used in such a way that different samples and reagents introduced from fluid inlets 11, 12 and 13 go through reagent-immobilized areas 30, 31 and 32 before the reaction solutions introduced from fluid inlet 10 go through reagent-immobilized areas 30, 31 and 32.

Next, practical use of the reaction vessel of the present invention is described with regard to an assay wherein the substance to be assayed is an antigen.

An assay of the antigen in the sample by sandwich method with the reaction vessel of FIG. 1a having an antibody immobilized therein may be carried out in accordance with the following procedure.

(1) A sample which is expected to contain the antigen to be assayed is introduced into channel 50 from fluid inlet 10 to allow for the antigen in the sample to bind to the antibody immobilized in reagent-immobilized area 30.

(2) A solution of a labelled antibody is introduced into channel 50 from fluid inlet 10 to allow for the labelled antibody to bind to the antigen which is bound to the antibody immobilized in reagent-immobilized area 30.

(3) After an optional washing with a washing solution, the presence or the quantity of the antigen is evaluated by means of the signal indicated by the label.

An assay by competitive method may be carried out by the following procedure.

(1) The sample is introduced into channel 50 from fluid inlet 10 to allow for the sample to be drawn through the capillary channel. The antigen, when present, binds to the antibody immobilized in the reagent-immobilized area 30.

(2) A solution of a labelled-antigen is introduced into channel 50 from fluid inlet 10 to allow for the labelled antigen to bind to the antibody immobilized in reagent-immobilized area 30.

(3) After an optional washing with a washing solution, the presence or the quantity of the antigen is evaluated by means of the signal indicated by the label.

It is to be noted that the sample and the labelled antibody in the case of the sandwich method or the sample and the labelled antigen in the case of the competitive method may be simultaneously introduced into the channel from the same fluid inlet.

The label used herein may be selected from commonly used labelling agents such as a dye, an isotope, an enzyme, and a fluorescent or luminescent substance. The binding of the label onto an antibody, an antigen or a hapten may be carried out by any desired method known in the art.

The signal indicated by the label may be measured by any desired conventional method. When the label is an enzyme, a substrate may be added to measure the enzyme activity. When the label is an isotope, the radiation activity may be measured. When the label is a dye, or a fluorescent or luminescent substance, the label may be measured by a suitable method.

An assay of the antigen in the sample by sandwich method with the reaction vessel of FIG. 2a having reagent-attached area 40 therein may be carried out in accordance with the following procedure.

(1) The sample is introduced into the channel from fluid inlet 10 so that the sample is drawn through capillary channel 52 to reach reagent-attached area 40 wherein a labelled antibody is attached. The antigen contained in the sample then binds to the labelled antibody to form an antigen-labelled antibody complex. The sample is further drawn through capillary channel 52 to reach reagent-immobilized area 30. The antigen-labelled antibody complex then binds to the antibody immobilized in reagent-immobilized area 30.

(2) After an optional washing with a washing solution, the presence or the quantity of the antigen is evaluated by means of the signal indicated by the label.

In the case of the competitive method, a reaction vessel having a labelled antigen attached in reagent-attached area 40 and an antibody immobilized in reagent-immobilized area 40 is used for the assay. As in the case of the sandwich method, the sample is introduced into the channel so that the sample will flow along the channel via reagent-attached area 40 to reagent-immobilized area 30. The antigen to be assayed and the labelled antigen which are both contained in the sample solution competitively bind to the antibody immobilized in the reagent-immobilized area 30. The results are evaluated by measuring the signal indicated by the label.

When an antigen is assayed by sandwich method in a reaction vessel shown FIGS. 3a, 3b, 3c, 3d, 3e and 3f having a fluorescence-labelled antibody attached in reagent-attached area 40, the sample is introduced into the channel from fluid inlet 10 and a buffer solution is introduced into the channel from fluid inlet 11. The antigen contained in the sample reaches reagent-immobilized area 30 and binds to the antibody immobilized in the area before the fluorescence-labelled antibody reaches reagent-immobilized area 30. The fluorescence-labelled antibody then reacts with the antigen bound to the antibody immobilized in area 30. After an optional washing with a washing solution, the results may be measured by measuring fluorescence intensity.

When an assay by sandwich method using an enzyme-labelled antibody is carried out in the reaction vessel of FIGS. 6a, 6b and 6c wherein a monoclonal antibody is immobilized in reagent-immobilized area 30 of the reagent immobilized zone X, an enzyme-labelled antibody is attached in reagent-attached area 40 of reagent attached zone S, and a substrate for the enzyme is attached in reagent-attached area 41 of reagent-attached zone T, the only procedure required for promoting various reactions involved in the assay is an introduction of the sample from fluid inlet 10. When the sample is introduced into the channel from fluid inlet 10, the antigen contained in the sample first binds to the enzyme-labelled antibody attached to reagent-attached area 40 of reagent-attached zone S to form an antigen-enzyme-labelled antibody complex. The antigen-enzyme-labelled antibody complex then binds to the monoclonal antibody immobilized in reagent-immobilized area 30 of reagent-immobilized zone X and becomes immobilized in area 30. When the substrate which was attached in reagent-attached area 41 of reagent-attached zone T reaches reagent-immobilized area 30, a signal such as a color change is exhibited in the area 30. The results may be evaluated by measuring such a signal.

A multi-item simultaneous assay may be carried out as described below by using the reaction vessel shown, for example, in FIG. 10. In this case, three types of antigens in the sample are simultaneously assayed by immobilizing three different antibodies which do not cross-react with each other onto reagent-immobilizing areas 30, 31 and 32.

(1) The sample is introduced into the channel from fluid inlet 10 to allow for the antigens in the sample to bind with the corresponding antibodies immobilized in reagent-immobilized areas 30, 31 and 32.

(2) A mixed solution of three different labelled antibodies is introduced into the channel from fluid inlet 10 to allow for each of the labelled antibodies to bind to the corresponding antigen bound to the antibody immobilized in either of reagent-immobilized areas 30, 31 and 32.

(3) After an optional washing with a washing solution, the results are evaluated by measuring the signal indicated by the label.

The labelling agents used for preparing the three different types of the labelled antibodies may be either the same or different from each other. The substance (antigen) in the sample to be assayed may be simultaneously assayed with a contrast substance contained in the sample when an antibody against the contrast substance as well as the antibody against the antigen to be assayed are immobilized in reagent-immobilized areas 30, 31 and 32.

Three different substances in the sample may also be simultaneously assayed with the reaction vessel of FIGS. 7a, 7b, 7c and 7d by the following procedure. When the substances in the sample to be assayed are three different antigens, an enzyme labelled-antibody against an antigenic determinant common to all of the three different antigens to be assayed is attached in reagent-attaching area 40 of reagent-attaching zone S, a substrate for the enzyme label is attached in reagent-attaching area 41 of reagent-attaching zone T, and an antibody against an antigenic determinant of the antigen which is uncommon to the three different antigens to be assayed is immobilized in each of reagent-immobilizing areas 30, 31 and 32 in reagent immobilizing zone X.

(1) A sample is introduced into the channel from fluid inlet 10 to fill the sample in fluid reservoir, wherein the sample is stirred if desired. The sample will then proceed through the channel into reagent-attached zone S wherein the three types of antigens to be assayed will bind to the enzyme-labelled antibody attached to reagent-attached area 40 to form three types of antigen-enzyme-labelled antibody complexes. When the sample solution proceeds into reagent-immobilized zone X, the antigen-enzyme-labelled antibody complexes will bind to the corresponding antibodies immobilized in reagent-immobilized areas 30, 31 and 32.

(2) The sample solution or a buffer solution is introduced into reagent-attached zone T from fluid inlet 11 to dissolve the substrate for the enzyme attached in reagent-attached area 41 of reagent-attached zone T. The thus dissolved substrate for the enzyme will reach reagent-immobilized zone S after the immobilization of the antigen-enzyme-labelled antibody complexes onto reagent-immobilized areas 30, 31 and 32.

(3) When the necessary reactions are completed, the reaction vessel will become inclined as shown in FIG. 7d with the downstream side of the reaction vessel moving downward in the direction indicated by the arrow in FIG. 7c. After an optional washing with a washing solution, the results are evaluated by measuring the signal indicated by the substrate.

The reaction vessel of this type is useful for assaying a small amount of sample such as serum taken from an infant.

It is to be noted that, in reagent-attaching area 40 of reagent-attaching zone S, three different enzyme labelled-antibodies against three different antigenic determinants which are not common to the three different antigens to be assayed may be attached instead of the enzyme labelled-antibody against an antigenic determinant common to all of the three different antigens. It is also to be noted that, although the description has been made with regard to the case wherein three substances in the sample are to be assayed, it is also possible to assay one or two substances by attaching or immobilizing one or two suitable reagents in reagent-immobilizing zone X and reagent-attached zone S, respectively.

The sample may be assayed simultaneously with a standard solution by using the reaction vessel shown, for example, in FIG. 11 according to the following procedure.

(1) The sample is introduced into the channel from fluid inlet 11, and the standard solutions of different concentration are introduced into the channel from fluid inlets 12 and 13. The antigen contained in the sample and the standard solutions then binds to the antibody immobilized in reagent-immobilized areas 30, 31 and 32. It is to be noted that the same antibody is immobilized in reagent-immobilizing areas 30, 31 and 32.

(2) A solution of a labelled antibody against the antigen to be assayed is introduced into the channel from fluid inlet 10 to allow for the labelled antibody to bind to the antigen bound to the antibody immobilized in reagent-immobilized areas 30, 31 and 32.

(3) After an optional washing with a washing solution, the results are evaluated by measuring the signal indicated by the label.

The reaction vessel of the present invention has been generally described in the foregoing. Preferred embodiments shown in the drawings are described in the following with brief description on their characteristic features.

The reaction vessel illustrated in FIGS. 1a and 1b is of the most simple construction.

The reaction vessel shown in FIGS. 2a, 2b and 2c has sub fluid reservoir 70, throat 60 and reagent-attached area 40 within its channel. Therefore, flow rate within the channel is controlled to secure a sufficient reaction time, and the frequency of introducing the reaction solutions is reduced.

The reaction vessel of FIGS. 3a, 3b and 3c has two fluid inlets 10 and 11. Therefore, a plurality of liquids can be introduced into the reaction vessel at a time.

The reaction vessel of FIGS. 4, 5, 6a, 6b, 6c, 7a, 7b, 7c, 7d, 8a, 8b, 8c, 8d, 8e, 9a9b and 9c are provided with fluid sump. Therefore, the fluids introduced into the reaction vessel do not flow out of the reaction vessel. The danger of contamination or infection is thus avoided.

In the reaction vessel of FIGS. 6a, 6b, 6c, 7a, 7b, 7c, 7d, 8a, 8b, 8c, 8d, 8e, 9a, 9b and 9c, the channel comprises an upstream portion including the fluid reservoir and a downstream portion including the fluid sump, and the upstream portion and the downstream portion are located in opposite sides of the center of gravity of the reaction vessel. Therefore, when the liquids introduced into the fluid reservoir from the fluid inlet have proceeded into the fluid sump with the predetermined reactions having been promoted in the channel to substantially complete the predetermined reactions, the structure of the reaction vessel becomes inclined with the side of the fluid sump moving downward as a consequence of the movement of the fluid from the upstream portion of the channel to the downstream portion of the channel. The inclination of the structure as described above is enabled by a rocking means. Referring to FIG. 6c, the rocking means is a pair of supports 9a. Referring to FIGS. 7c and 7d, the rocking means is a curved lower major surface of the structure. Referring to FIG. 8d, the rocking means is a plate.

The reaction vessel of FIGS. 6a, 6b and 6c has an advantage that the introduction of the sample is the only operation required for completing all the necessary reactions. The reaction vessel of this type is easy to mold since fluid outlet 20 is located at the position indicated in FIG. 6b to enable a smooth release of the molded segment from the mold.

The reaction vessel of FIGS. 7a, 7b, 7c and 7d has advantages that a simultaneous multi-item assay may be carried out with a minute amount of the sample, and that a high reaction precision is achieved through precise control of the flow rate by accommodating hydrophilic thread 49 in at least a part of the channel. The reaction vessel of this type also has mold release properties equivalent to the reaction vessel of FIGS. 6a, 6b and 6c.

The reaction vessel of FIGS. 8a, 8b, 8c, 8d and 8e has advantages that the introduction of the sample is the only operation required for completing all the necessary reactions, and that two substances may be assayed at a time. A precise control of the flow rate along the channel is also enabled by accommodating hydrophilic thread 59 in a part of the channel as in the case of FIGS. 7a, 7b, 7c and 7d.

The reaction vessel shown in FIGS. 9a, 9b and 9c has an advantage that a sufficient time is provided for the reaction between the substance to be assayed and the reagent immobilized in reagent-immobilized zone X.

The reaction vessels of FIGS. 10 and 12 are adapted for a simultaneous multi-item assay despite their simple structure.

The reaction vessel of FIG. 11 has an advantage that, when used for a simultaneous multi-item assay, substances which interfere with each other may be assayed at a time. The reaction vessel of this type may also be used for assaying a plurality of different samples at a time.

The reaction vessels shown in FIGS. 20 and 21 are adapted for assaying a plurality of items or a plurality of samples at a time, and therefore, are useful for group examination.

As set forth above, the reaction vessel of the present invention has a wide variety of construction, and therefore, may be used for assays of different kinds.

The reaction vessel of the present invention may be used for an automatic assay as well as a manual assay. For example, the reaction vessel of the present invention may be used for an automatic assay by loading the reaction vessel on conveyer means of the chemical reaction apparatus of Japanese Patent Application Kokai No. 63-69539 instead of a capillary tube.

More illustratively, the reaction vessel of the present invention having an antibody immobilized in the channel and an enzyme-labelled antibody attached in the channel is loaded on an apparatus having a conveyer means such as a belt conveyer, a means for supplying sample, reagent and washing solutions, and a measuring means such as an optical means. A sample which is expected to contain an antigen, a washing solution, and a solution of a substrate for the enzyme are sequentially into the reaction vessel with an automatic dispenser. The color indicated by the substrate is then measured by photometer. The withdrawal of the liquids introduced into the reaction vessel may be carried out by suction. If desired, the measurements may be analyzed with a computer to use the results as an aid for a diagnosis.

The present invention will be described in further detail by referring to non-limiting Examples.

EXAMPLES

EXAMPLE 1

A pregnancy test employing a reaction vessel having a configuration of FIGS. 2a, 2b and 2c is carried out as described below.

(1) PREPARATION OF THE REACTION VESSEL

A monoclonal anti-hCG (human chorionic gonadotropin) antibody is immobilized on reagent-immobilizing area 30 in capillary channel 52 of the channel provided in lower segment 5, which comprises a white plastic resin (polyacrylic resin), by a process known for binding an antibody on an insoluble carrier.

Next, a solution (50 $\mu$g/ml) of a monoclonal anti-hCG antibody which has been labelled with alkaline phosphatase (hereinafter referred to as labelled antibody A) is pipetted onto reagent-attaching area 40 in capillary channel 52 of the channel provided in segment 5.

After lyophilizing the antibody, upper segment 4, which comprises a colorless transparent plastic resin (a polyacrylic resin), is bonded to segment 5.

Capillary channels 51 and 52 have a width of 3 mm and a depth of 0.2 mm.

(2) Measurement

A small quantity of urine from a pregnant woman is collected in a pipette, and the thus collected urine is pipetted into the reaction vessel 1 from fluid inlet 10 to fill fluid reservoir 70 with the urine. The urine gradually passes through capillary channel 51 and moves into capillary channel 52 with its speed being controlled at throat 60 of the channel. The urine passes through capillary channel 52 to reach reagent-attached area 40, upon which labelled antibody A which has been tentatively attached to area 40 dissolves into the urine and binds to the hCG contained in the urine to form an hCG-labelled antibody A complex.

The urine is further drawn through capillary channel 52 to reach reagent-immobilized area 30 onto which the monoclonal anti-hCG antibody has been immobilized, whereupon the hCG-labelled antibody A complex binds to the immobilized monoclonal anti-hCG antibody and become immobilized on area 30. The urine containing a large quantity of excess labelled antibody A which failed to bind to the immobilized monoclonal anti-hCG antibody on area 30 is then drawn through capillary channel 52 to outlet 20. It is to be noted that, when fluid reservoir 70 becomes empty, the urine will no longer be introduced into capillary channels 51 and 52.

Next, fluid reservoir 70 is filled with a solution of BCIP (5-bromo-4-chloro-3-indolyl phosphate), which is a chromogenic substrate for the enzyme label, (hereinafter referred to as substrate solution A). Substrate solution A is then drawn through capillary channels 51 and 52, whereby the urine is completely discharged from the reaction vessel.

When substrate solution A reaches reagent-immobilized area 30, BCIP develops a blue color by the function of the enzyme which has been immobilized in this area. The blue color development is an indication of the presence of hCG in the urine which allows for the pregnancy to be detected.

When a urine from a non-pregnant woman, in which hCG is absent, is used for the test, enzyme-labelled antibody A will not be immobilized in reagent-immobilized area 30, and will be discharged from outlet 20. In such a case, reagent-immobilized area 30 will not exhibit any color-development upon contact with the substrate solution A.

EXAMPLE 2

A pregnancy test employing a reaction vessel having a configuration similar to the one depicted in FIGS. 3a, 3b, 3c, 3d, 3e and 3f is carried out as described below. The reaction vessel employed had a reagent attached in fluid reservoir 70 in addition to reagent-attached area 40, defining another reagent-attached area.

(1) PREPARATION OF THE REACTION VESSEL

A monoclonal anti-hCG antibody is immobilized on reagent-immobilizing area 30 in capillary channel 54 of the channel provided in segment 5 by a process known for binding an antibody on an insoluble carrier. Segment 5 comprises a white plastic resin (polystyrene resin). (See FIG. 3c.)

Next, a solution of the above-mentioned labelled antibody A (100 $\mu$g/ml) is carefully pipetted into fluid reservoir 70 such that no solution is drawn to further than throat 60, and thereafter, the antibody is lyophilized.

In the meanwhile, the above mentioned substrate solution A (10 $\mu$g/ml) is also pipetted onto reagent-attaching area 40 in capillary channel 52 of the channel in segment 4. Segment 4 comprises a white plastic resin except for portion 7 corresponding to reagent-immobilized area 40, which comprises a transparent plastic resin. Substrate solution A is then lyophilized (see FIG. 3b).

Segment 4 is adhered to the thus treated segment 5, and then, to segment 4 is adhered lid segment 3 comprising a plastic resin (polystyrene resin). Segment 3 is white except for portion 6 corresponding to reagent-immobilized area 40, which is transparent.

Capillary channels 51, 52, 53 and 54 have a width of 2 mm and a depth of 0.2 mm.

(2) Measurement

A small quantity of urine from a pregnant woman is collected in a pipette, and the thus collected urine is pipetted into fluid inlet 10 to fill fluid reservoir 70 with the urine and to thereby dissolve labelled antibody A which has been attached to fluid reservoir 70 into the urine. The urine which is identical to the one pipetted into fluid inlet 10 is pipetted into another fluid inlet 11 to fill another fluid reservoir 71 with the urine.

The urine in fluid reservoir 70 is gradually drawn into capillary channel 54 through throat 60 and passes through capillary channel 54, while the hCG contained in the urine becomes bound to labelled antibody A dissolved in the urine from fluid reservoir 70 to form an hCG-labelled antibody A complex. When the urine reaches reagent-immobilized area 30, the hCG-labelled antibody A complex is caught by the monoclonal anti-hCG antibody immobilized in this area, whereby the complex becomes immobilized to this area. The urine containing a large quantity of excess labelled antibody A which failed to bind to the monoclonal anti-hCG antibody immobilized in area 30 is further drawn through capillary channel 54 to outlet 20.

In the meanwhile, the urine in fluid reservoir 71 is drawn into capillary channel 52 through throat 61, and passes through capillary channel 52 along the winding channel to reach reagent-attached area 40 whereupon the urine dissolves BCIP, which is the substrate for the enzyme label as described above. The urine is then drawn into capillary channel 54 through communicating channel 56 (57). Since capillary channel 52 has a total length significantly larger than that of capillary channel 54, the urine having the substrate dissolved therein reaches reagent-immobilized area 30 after the urine having enzyme-labelled antibody A dissolved therein has all passed through the reagent-immobilized area 30.

When the urine having the substrate dissolved therein reaches reagent-immobilized area 30, the substrate develops a blue color with the lapse of time by the function of the enzyme immobilized in this area to indicate the presence of hCG in the urine, confirming the pregnancy of the individual from which the sample had been collected. The color development in reagent-immobilized area 30 may be checked through transparent portions 6 and 7 of segments 3 and 4. When hCG is absent in the urine, labelled antibody A will not be immobilized to reagent-immobilized area 30, and will flow out of the reaction vessel from outlet 20. In such a case, reagent-immobilized area 30 will not exhibit any blue color as in the case of pregnant urine.

EXAMPLE 3

Three types of tumor markers are automatically and simultaneously measured by employing a reaction vessel shown in FIG. 20 as described below.

(1) PREPARATION OF THE REACTION VESSEL

The reaction vessel comprises an upper lid segment and a lower segment, and has a plurality of reaction units each comprising a channels 50 therein. The lower segment comprises a white plastic resin (polystyrene resin). The three types of tumor markers to be measured are hCG, CEA and alpha-fetoprotein. Monoclonal antibodies against each of the three tumor markers are immobilized on lower segment in reagent-immobilizing areas 30, 31 and 32 in capillary channel 51 in channel 50 of one unit by a process known for binding an antibody on an insoluble carrier. The antibodies against the three tumor markers are also immobilized in channels 50 of other units by the same manner.

To the above-described lower segment is adhered the upper segment comprising a colorless transparent plastic resin (polystyrene resin) to provide reaction vessel 1.

The thus prepared reaction vessel 1 has ten parallel channels 50 each having a width of 3 mm and a depth of 0.3 mm.

(2) AUTOMATIC MEASURING SYSTEM

The system used herein comprises conveyor means for moving the reaction vessel in two perpendicular directions at regular pitches, feed means for supplying the reaction vessel with samples, reagents, washing solution and the like, suction means for drawing the fluid in the capillary channel from the outlet, and optical means for measuring the color development.

The automatic system used herein, except for its optical means, has a structure capable of treating 10 samples at a time.

(3) Measurement

The reaction vessel is located on the conveyor means of the automatic system.

The reaction vessel is conveyed to a predetermined position at which ten sample-feed nozzles simultaneously supply human serum sample Nos. 1 to 10 to the reaction vessel. Each sample is fed to channel 50 from fluid inlet 10, and drawn through capillary channel 51 to reagent-immobilized areas 30, 31 and 32 wherein antibodies against each of the three types of the tumor markers have been immobilized. The substances to be measured, which are the tumor markers, are caught by the corresponding immobilized antibodies, and become immobilized to the corresponding areas.

In five minutes, the reaction vessel is conveyed to a position where the washing solution is supplied. At this position, human serum sample Nos. 1 to 10 are withdrawn from channels 50 through outlets 20 by suction. The washing solution is then fed to channels 50 and again withdrawn from outlets 20 by suction. The washing/suction operation is repeated five times.

The reaction vessel will then be conveyed to a position where a reagent is supplied. At this position, the reaction vessel is supplied with a buffer solution having dissolved therein enzyme-labelled antibodies (which in this case are a mixture of antibodies against the above-mentioned hCG, CEA and alpha-fetoprotein which have been labelled with alkaline phosphatase).

The enzyme-labelled antibodies bind to their corresponding tumor markers, which have been bound to antibodies immobilized on reagent-immobilized areas 30, 31 and 32. The enzyme-labelled antibodies thus become immobilized on the corresponding reagent-immobilized areas 30, 31 and 32. The enzyme-labelled antibodies will not bind to the antibody which has no tumor marker bound thereto.

In five minutes, the reaction vessel is conveyed to another position where the washing solution is supplied. At this position, the solution containing the enzyme-labelled antibodies is withdrawn from channels 50 through outlets 20 by suction. The washing solution is then fed to channels 50 and again withdrawn from outlets 20 by suction. The washing/suction operation is repeated five times.

Upon completion of the washing/suction operation, the reaction vessel is conveyed to a position where another reagent is supplied. At this position, substrate solution A as described above is fed to each channel 50.

In this example, the sample serums contain tumor markers and the enzyme-labelled antibodies are immobilized in the corresponding reagent-immobilized areas, and therefore, the substrate will develop blue colors within the reagent-immobilized areas. The blue color developed in each area will have a strength proportional to the concentration of the tumor marker contained in the sample serum.

The reaction vessel is then conveyed to a position where the colors developed in reagent-immobilized areas 30, 31 and 32 are measured by the optical means to quantitatively determine the amounts of the tumor markers contained in each sample serum.

The automatic measuring system is capable of sequentially handling a plurality of reaction vessels, and therefore, a large number of serum samples may be automatically treated.

EXAMPLE 4

Three types of tumor markers are automatically and simultaneously measured by employing a reaction vessel shown in FIG. 21 as described below.

(1) PREPARATION OF THE REACTION VESSEL

The reaction vessel 1 comprises an upper segment and a lower segment, and has a plurality of reaction units including first and second reaction units 100 and 200. Each reaction unit comprises a branched channel including capillary channels 51, 52, 53 and 54. Three types of tumor markers to be measured are hCG, CEA and alpha-fetoprotein. Monoclonal antibodies against each of the three tumor markers are immobilized on lower segment of the reaction vessel in reagent-immobilizing areas 30, 31 and 32 in capillary channels 52, 53 and 54, respectively, by a process known for binding an antibody on an insoluble carrier. This lower segment comprises a white plastic resin (polystyrene resin). The antibodies against the three tumor markers are also immobilized on other reaction units including second reaction unit 200 by the same manner.

To the above-described lower segment is adhered the upper segment comprising a colorless transparent plastic resin (polystyrene resin) to provide reaction vessel 1.

Capillary channels 51, 52, 53 and 54 of the branched channel of the thus prepared reaction vessel 1 have a width of 5 mm and a depth of 0.5 mm.

(2) AUTOMATIC MEASURING SYSTEM

The system used herein comprises conveyor means for moving the reaction vessel at regular pitches, feed means for supplying the reaction vessel with samples, reagents, washing solution and the like, and suction means for drawing the fluid in the capillary channel from the outlet.

(3) Measurement

The reaction vessel is located on the conveyor means of the automatic system.

The reaction vessel is conveyed to a predetermined position at which the sample feed means supply human serum sample No. 1 to first reaction unit 100. The sample serum is fed from fluid inlet 10 to capillary channel 51 of the branched channel.

The sample serum is then drawn through capillary channel 51 to capillary channels 52, 53 and 54, and reaches reagent-immobilized areas 30, 31 and 32 wherein antibodies against each of the three types of the tumor markers have been immobilized. The substances to be measured, which are the tumor markers, are caught by the corresponding immobilized antibodies, and become immobilized to the corresponding areas.

In 2.5 minutes, the reaction vessel is conveyed to a position at which fluid inlet 10 of first reaction unit 100 is situated below washing solution feed means A and fluid inlet 10 of second reaction unit 200 is situated below sample feed means. At this position, the sample feed means supply human serum sample No. 2 to capillary channel 51 of second reaction unit 200 through fluid inlet 10 of second reaction unit 200. In the meanwhile, human serum sample 1 is withdrawn from first reaction unit 100 through fluid outlets 20, 21 and 22 by suction, and feed of the washing solution to fluid inlet 10 of first reaction unit 100 and withdrawal of the washing solution from outlets 20, 21 and 22 of reaction unit 100 by suction are subsequently repeated five times.

In 2.5 minutes calculated from completion of the withdrawal of human serum sample No. 1 from first reaction unit 100 by suction, the reaction vessel is conveyed to a position at which fluid inlets 11, 12 and 13 of first reaction unit 100 is situated below reagent feed means A and and fluid inlet 10 of third reaction unit (not shown) is situated below sample feed means. At this position, buffer solutions having dissolved therein each of antibodies against hCG, CEA and alpha-fetoprotein labelled with alkaline phosphatase are fed to fluid inlets 11, 12 and 13 of first reaction unit 100, respectively.

The enzyme-labelled antibodies binds to their corresponding tumor markers, which are bound to antibodies immobilized on reagent-immobilized areas 30, 31 and 32. The enzyme-labelled antibodies thus become immobilized on the corresponding reagent-immobilized areas 30, 31 and 32. The enzyme-labelled antibodies will not bind to the antibody which has no tumor marker bound thereto.

In 2.5 minutes calculated from completion of the feeding of the enzyme-labelled antibody to reaction unit 100, the reaction vessel is conveyed to a position at which fluid inlet 10 of first reaction unit 100 is situated below washing solution feed means B and and fluid inlet 10 of fourth reaction unit (not shown) is situated below sample feed means. At this position, the buffer solutions containing the enzyme-labelled antibodies are withdrawn from outlets 20, 21 and 22 of reaction unit 100 by suction. The washing solution is then fed to inlet 10 of reaction unit 100 and withdrawn from outlets 20, 21 and 22 of reaction unit 100 by suction. The washing/suction operation is repeated five times.

In 2.5 minutes calculated from completion of the withdrawal of the buffer solutions containing the enzyme-labelled antibodies from first reaction unit 100 by suction, the reaction vessel is conveyed to a position at which fluid inlet 10 of first reaction unit 100 is situated below reagent feed means B and and fluid inlet 10 of fifth reaction unit (not shown) is situated below sample feed means. At this position, substrate solution A as described above is fed to the reaction vessel 1 from fluid inlet 10 of first reaction unit 100.

In this example, the sample serum contains tumor markers and the enzyme-labelled antibodies are immobilized to their corresponding reagent-immobilized areas, and therefore, the substrate will bind to the enzyme label to develop blue colors within the reagent-immobilized areas.

In 2.5 minutes calculated from completion of the feeding of substrate solution A to first reaction unit 100, the reaction vessel is conveyed to a position at which fluid inlet 10 of first reaction unit 100 is situated below washing solution feed means C and and fluid inlet 10 of sixth reaction unit (not shown) is situated below sample feed means. At this position, substrate solution A is withdrawn from outlets 20, 21 and 22 of reaction unit 100 by suction. The washing solution is then fed to inlet 10 of reaction unit 100 and withdrawn from outlets 20, 21 and 22 of reaction unit 100 by suction. The washing/suction operation is automatically repeated five times. Since the blue colors developed by substrate solution A remain after withdrawal of the substrate solution, the determination of the presence/absence of the tumor markers in the sample serum may be carried out by observing reagent-immobilized areas 30, 31, and 32 with unaided eye at this stage.

It is to be noted that other sample serums fed to other reaction units including second reaction unit 200 will likewise be treated.

EXAMPLE 5

A diagnosis of hepatitis B is carried out by employing a reaction vessel having a configuration of FIGS. 2a, 2b and 2c as described below.

(1) PREPARATION OF THE REACTION VESSEL

A heat-denatured solution (5 μg/ml) containing a DNA fragment corresponding to the DNA of hepatitis B virus is prepared. 20 μg of the solution is pipetted onto reagent-immobilizing area 30 in capillary channel 52 in lower segment 5, which comprises a white plastic resin (polyacrylic resin). The solution is allowed to stand at 25° C. for 24 hours, and then withdrawn therefrom by suction. Area 30 is then irradiated with UV for the purpose of immobilizing the DNA fragment on area 30.

Next, 10 μl of a solution (0.02 μg/ml) of a probe for the DNA of hepatitis B virus which has been labelled with biotin is pipetted onto reagent-attaching area 40 in capillary channel 52 provided in segment 5.

After lyophilization, segment 4, which comprises a colorless transparent plastic resin (a polyacrylic resin), is bonded to segment 5.

Capillary channels 51 and 52 have a width of 3 mm and a depth of 0.2 mm.

(2) Measurement

DNA sample was extracted from serum of a patient suffering from hepatitis.

The sample is pipetted into the reaction vessel 1 from fluid inlet 10 to fill fluid reservoir 70 with the sample. The sample gradually passes through capillary channel 51 and moves into capillary channel 52 with its speed being controlled at throat 60 of the channel. The sample passes through capillary channel 52 to reach reagent-attached area 40, upon which the biotin-labelled DNA probe which has been tentatively attached in the area 40 dissolves into the sample. The sample is further drawn through capillary channel 52 while the biotin-labelled DNA probe binds to the hepatitis B virus contained in the sample to form a complex of the biotin labelled DNA probe and the hepatitis virus B.

The sample then reaches reagent-immobilized area 30, upon which the complex of the biotin-labelled DNA probe and the hepatitis virus B in the sample binds to the DNA fragment corresponding to the hepatitis B virus immobilized on area 30, and become immobilized on area 30. The sample containing a large quantity of excess biotin-labelled probe which failed to bind to area 30 is then drawn through capillary channel 52 to outlet 20. It is to be noted that, when fluid reservoir 70 becomes empty, the sample will no longer be introduced into capillary channels 51 and 52.

Next, fluid reservoir 70 is filled with a preliminarily prepared solution (100 μg/ml) of avidin-biotin-labelled peroxidase complex by pipetting the solution into fluid inlet 10. The solution of the avidin-biotin-labelled peroxidase complex is then drawn through capillary channels 51 and 52, whereby the sample is completely discharged from the reaction vessel.

When the solution of the avidin-biotin-labelled peroxidase complex reaches reagent-immobilized area 30, the avidin-biotin-labelled peroxidase complex binds to the biotin which has been immobilized on area 30, and become immobilized on area 30. The solution containing the excess avidin-biotin-labelled peroxidase complex is further drawn through capillary channel 52 to outlet 20. It is to be noted that, when fluid reservoir 70 becomes empty, the solution will no longer be introduced into capillary channels 51 and 52.

Next, fluid reservoir 70 is filled with a 0.076 M phosphate-buffered saline, pH 7.0 (hereinafter referred to as PBS) by pipetting the PBS into fluid inlet 10. The PBS is then gradually drawn through capillary channel 51, throat 60 and capillary channel 52 to thereby discharge the solution of the avidin biotin-labelled peroxidase complex out of the reaction vessel. When the PBS reaches reagent-immobilized area 30, the area is washed with the PBS. The PBS is further drawn through capillary channel 52 to outlet 20. It is to be noted that, when fluid reservoir 70 becomes empty, the PBS will no longer be introduced into capillary channels 51 and 52.

When fluid reservoir 70 becomes empty, a mixed solution of hydrogen peroxide, which is the substrate for the peroxidase, and o-phenylenediamine, which is a chromogen is subsequently introduced into fluid reservoir 70. The solution is drawn through capillary channels 51 and 52 to thereby discharge the PBS out of the reaction vessel.

When the solution reaches reagent-immobilized area 30, the chromogenic o-phenylenediamine develops a yellow color by function of the peroxidase immobilized on area 30. The development of the yellow color indicates presence of hepatitis B virus in the serum sample, and therefore, a strong contagiousness of the serum sample. When hepatitis B virus is absent in the serum sample, the enzyme will be totally discharged from fluid outlet 20 without being caught in area 30. In such a case, no color development will be observed in area 30.

EXAMPLE 6

Luteinizing hormone (LH) is detected by employing the reaction vessel shown in FIGS. 8a, 8b, 8c, 8d and 8e.

Segments 3, 4 and 5 of the reaction vessel is molded from a colorless transparent plastic resin (epoxy resin). Capillary channels 51, 52, 53, 54 and 55 have a width of 0.7 mm and a depth of 0.7 mm. A cotton thread having a circular cross section with a diameter of 0.5 mm, which is hydrophilic thread 59, is stretched in capillary channel 55 of the channel defined in segment 4 between water-absorbent material-accommodating area 80 and reagent-immobilizing area 31, and fixed thereto by an adhesive. Capillary channel 55 includes hollow chamber 58.

On reagent-immobilizing area 30 of reagent-immobilizing zone X, which is defined in a channel provided on lower major surface of segment 4, an anti-LH-β antibody is immobilized by a method known for immobilizing an antibody to an insolubilized carrier. Segment 5 is then adhered to the lower major surface of segment 4. On reagent-immobilizing area 31 of reagent-immobilizing zone X, which is defined in a channel provided on upper major surface of segment 4, is immobilized an anti-mouse IgG antibody by a method known for immobilizing an antibody to an insolubilized carrier.

On reagent-attaching area 40 of reagent-attaching zone S in segment 4, 0.5 ml of a solution (10 μg/ml) of a monoclonal anti-LH-α antibody labelled with alkaline phosphatase (hereinafter referred to as labelled antibody B) is pipetted.

Further, onto reagent-attaching areas 41 of reagent-attaching zone T in segment 4, substrate solution A (2 mg BCIP/ml) as mentioned above is pipetted, and thereafter, the reagents are lyophilized.

Next, 30 mg of nonwoven fabric (absorbent material 81) is accommodated in absorbent material-accommodating area 80 of segment 4. Segment 3 is adhered to the upper surface of segment 4, and then, plate 9b is adhered to the lower surface of segment 5.

(2) Measurement

50 μl of a sample urine is collected in a pipette, and pipetted into fluid inlet 10 to fill fluid reservoir 70 with the urine. The urine gradually passes through capillary channel 51 and moves into capillary channel 52 to reach reagent-attached zone T, upon which the substrate BCIP which has been tentatively attached to this zone dissolves into the urine.

Once reagent-attached zone T is filled with the urine, the urine is then drawn to reagent-attached zone S to dissolve labelled antibody B tentatively attached to this area. The LH in urine then binds to the labelled antibody B to form a complex of LH and labelled antibody B, namely, an LH-labelled anti-LH-α antibody complex The urine is further drawn through capillary channel 53, reagent-immobilized area 30, capillary channel 54, reagent-immobilized zone 31, and cotton thread (hydrophilic thread 59) to reach absorbent material-accommodated area 80, wherein the urine is absorbed and retained in the nonwoven fabric (absorbent material 81). In this process, the LH-labelled anti-LH-α antibody complex contained in the urine binds to the anti-LH-β antibody immobilized on reagent-immobilized zone 30 as well as the anti-mouse IgG antibody immobilized on reagent-immobilized area 31. Consequently, the LH-labelled anti-LH-α antibody complex is immobilized on both areas 30 and 31.

When fluid reservoir 70 becomes empty, the urine having dissolved therein the substrate flows out of reagent-attached area T, and is drawn through capillary channels 52 and 51, reagent-attached zone S, capillary channel 53, reagent-immobilized area 30, capillary channel 54, reagent-immobilized zone 31, and cotton thread (hydrophilic thread 59) to reach absorbent material-accommodated area 80, wherein the urine is absorbed and retained in the nonwoven fabric (absorbent material 81). In this process, the substrate develops blue colors by function of the enzyme immobilized in both reagent-immobilized areas 30 and 31, and reagent-immobilized zone X exhibit "+". The indication of "+" enables to determine that the test result is positive, namely, that LH is present in the sample urine.

On the other hand, when a urine free of LH is used as a sample, labelled antibody will be immobilized only on reagent-immobilized area 31, and will not be immobilized on reagent-immobilized area 30. In this case, the substrate develops a blue color only at reagent-immobilized area 31 by the function of the enzyme immobilized in area 31, while reagent-immobilized area 30 fails to develop such a color. As a consequence, reagent-immobilized zone X exhibits "−".

The total reaction time required is about 5 minutes, and the concentration of LH required for the indication of "+" is 50 mIU/ml.

As described above, the present invention provides reaction vessels which enable a highly sensitive measurement to be carried out with an accurate and convenient B/F separation.

The reaction vessels in accordance with the present invention are quite useful. They have a wide variety of applications including detections utilizing varying reactions such as enzyme immunoassays and those utilizing nucleic acid hybridization. They can also be used for multi-item measurements by simple and convenient operation. They can be used for both measurements with or without automatic measuring system.

The reaction vessels in accordance with the present invention may be used not only for qualitative determinations but also for quantitative determinations. In particular, the reaction vessels of the invention are quite useful since they can carry out simple and convenient quantitative measurements, which have been difficult to carry out with conventional reaction vessels.

It should be understood that the foregoing description is for the purpose of illustration and that the invention includes modifications and equivalents within the scope of the appended claims.

We claim:

1. A fluid circuit reaction vessel for detecting a target substance contained in a minute amount in a fluid sample, wherein said vessel comprises:
   (A) a body structure, said body structure comprising an upstream portion on one side of a center of gravity of the body structure and a downstream portion on the other side of the center of gravity of the body structure;
   (B) a fluid circuit defined in said body structure, said fluid circuit comprising,
      (a) at least one fluid inlet for introducing at least one fluid including the fluid sample containing the target substance, said fluid inlet being provided in the upstream portion of the body structure,
      (b) at least one fluid sump provided in the downstream portion of the body structure,
      (c) at least one fluid channel connecting said fluid inlet and said fluid sump,
      (d) at least one reagent-immobilized area provided in said fluid channel, said reagent-immobilized area having a reagent fixedly immobilized thereto, said reagent being able to specifically react with said target substance contained in the sample,
      (e) at least one reagent-attached area provided in said fluid channel between said fluid inlet and said reagent immobilized area, said reagent-attached area having a reagent reversibly attached thereto, and (f) a vent mechanism comprising at least one ventilatory outlet provided in said fluid circuit for venting said fluid circuit; and (g) a rocking means for allowing said body structure to become inclined with said downstream portion of the body structure including said fluid sump moving downward to indicate substantial completion of the detection, said inclination being induced by the movement of the fluid into said fluid sump.

2. The reaction vessel according to claim 1, wherein said rocking means is selected from the group consisting of
(a) the body structure having a pair of supports on a lower major surface thereof,
(b) the body structure having a plate on a lower major surface thereof, and
(c) the body structure having a curved lower major surface.

3. The reaction vessel according to claim 1, wherein said fluid sump comprises said fluid channel capable of holding the fluid which has undergone the detection.

4. The reaction vessel according to claim 1, wherein at least one of said reagent-immobilized area and said reagent-attached area is in the form of at least one of a recess and a group of protrusions.

5. The reaction vessel according to claim 1, wherein said circuit has at least one fluid reservoir in communication with said fluid inlet.

6. The reaction vessel according to claim 1, wherein at least a portion of said channel extends vertically.

7. The reaction vessel according to claim 1, wherein said channel comprises a capillary channel.

8. The reaction vessel according to claim 1, wherein said channel has a throat having a smaller diameter than the rest of the channel.

9. The reaction vessel according to claim 1, wherein said fluid channel is dilated in at least one of said reagent-immobilized area and said reagent-attached area.

10. The reaction vessel according to claim 1, wherein at least a part of said fluid circuit comprises a hydrophilic material.

11. The reaction vessel according to claim 1, wherein said fluid circuit comprises one fluid inlet, said fluid sump and one fluid channel, and a plurality of non-cross-reacting reagents are immobilized in said channel.

12. The reaction vessel according to claim 1, wherein said fluid circuit comprises one fluid inlet and two or more fluid sumps, and the fluid channel is branched to connect said one fluid inlet and said two or more fluid sumps, and wherein the reagent-immobilized area is provided in each branch of the branched channel.

13. The reaction vessel according to claim 1, wherein said reaction vessel has two or more fluid circuits, arranged in rows.

14. The reaction vessel according to claim 1, wherein said fluid sump has a water-absorbent material accommodated therein.

15. The reaction vessel according to claim 14, wherein said water-absorbent material is an absorbent wadding.

16. The reaction vessel according to claim 1, wherein a thread of a hydrophilic material is accommodated in at least one portion of said channel between said reagent-immobilized area and said fluid sump.

17. The reaction vessel according to claim 16, wherein at least a part of said hydrophilic thread is stretched in a non-capillary hollow chamber defined in said channel.

18. The reaction vessel according to claim 1, wherein said body structure comprises at least one segment having the fluid circuit defined therein.

19. The reaction vessel according to claim 18, wherein said structure comprises at least first, second and third adjacent segments and said at least one channel comprises a first channel defined between said first and second adjacent segments and a second channel defined between said second and third adjacent segments, wherein the first and second channels are in communication with each other.

20. The reaction vessel according to claim 18, wherein said body structure comprises a lid segment in addition to the segment having the fluid circuit defined therein.

21. The reaction vessel according to claim 20, wherein said segment having the fluid circuit defined therein is in close contact with said lid segment.

22. The reaction vessel according to claim 20, wherein an intervening space is defined between said segment having the fluid circuit defined therein and said lid segment.

* * * * *